US007026528B2

(12) United States Patent
Cheng et al.

(10) Patent No.: US 7,026,528 B2
(45) Date of Patent: Apr. 11, 2006

(54) METHODS FOR THE PRODUCTION OF STABLY-TRANSFORMED, FERTILE WHEAT EMPLOYING AGROBACTERIUM-MEDIATED TRANSFORMATION AND COMPOSITIONS DERIVED THEREFROM

(75) Inventors: Ming Cheng, St. Louis, MO (US); Joyce E. Fry, St. Louis, MO (US); Yeuchun Wan, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 412 days.

(21) Appl. No.: 10/210,370

(22) Filed: Jul. 31, 2002

(65) Prior Publication Data

US 2003/0024014 A1    Jan. 30, 2003

Related U.S. Application Data

(63) Continuation of application No. 09/234,974, filed on Jan. 21, 1999, now abandoned, which is a continuation of application No. 08/667,188, filed on Jun. 21, 1996, now abandoned.

(51) Int. Cl.
*C12N 15/82* (2006.01)
*A01H 4/00* (2006.01)

(52) U.S. Cl. .................... 800/294; 435/469; 435/430.1
(58) Field of Classification Search ................ 435/419, 435/468, 469, 430.1; 800/294, 320.3
See application file for complete search history.

(56) References Cited

U.S. PATENT DOCUMENTS

| 5,306,863 | A | 4/1994 | Hilder et al. | ................ | 800/205 |
| 5,482,852 | A | 1/1996 | Yoder et al. | ............. | 435/172.3 |
| 5,484,956 | A | 1/1996 | Lundquist et al. | .......... | 800/205 |
| 5,489,520 | A | 2/1996 | Adams et al. | ........... | 435/172.3 |
| 5,508,468 | A | 4/1996 | Lundquist et al. | .......... | 800/205 |
| 5,591,616 | A | 1/1997 | Hiei et al. | ................ | 435/172.3 |
| 6,020,539 | A | 2/2000 | Goldman et al. | ........... | 800/294 |
| 6,037,526 | A | 3/2000 | Grimsley et al. | ........... | 800/300 |

FOREIGN PATENT DOCUMENTS

| AU | 57356/86 | 5/1986 |
| AU | 80893/87 | 11/1987 |
| AU | 31076/89 | 3/1989 |
| AU | 45134/93 | 1/1994 |
| DE | 4309203 | 4/1994 |
| EP | 0586355 A2 | 8/1993 |
| EP | 0604662 | 7/1994 |
| EP | 0672752 | 9/1995 |
| EP | 0709462 | 5/1996 |
| JP | 75460/94 | 3/1995 |
| WO | WO 89/12102 | 12/1989 |
| WO | WO 91/02071 | 2/1991 |
| WO | WO 92/06205 | 4/1992 |
| WO | WO 92/13957 | 8/1992 |
| WO | WO 93/04178 | 3/1993 |
| WO | WO 93/18168 | 9/1993 |
| WO | WO 94/00583 | 1/1994 |
| WO | WO 94/00977 | 1/1994 |
| WO | WO 94/13822 | 6/1994 |
| WO | WO 95/06722 | 9/1995 |

OTHER PUBLICATIONS

Hood E. et al. May 1994. Agrobacterium mediated transformation of wheat. Plant Physiology Supplement, vol. 105, No. 1, pag 114.*
Hess D et al. Transformation experiments by pipetting Agrobacterium into the spikelets of wheat (Triticum aestivum L.) 1990, Plant Science, vol. 72, pp. 233-244.*
Evidence-in-Support Statutory Declaration of Rachel Anita Burton (and supporting exhibits, Exhibits A and B), executed Sep. 27, 2002.
Evidence-in-Support Statutory Declaration of Philip John Larkin (and supporting exhibit, Exhibits PJL-1), executed Oct. 17, 2002.
Evidence-in-Support Statutory Declaration of Richard Ian Scott Brettell (and supporting exhibits, Exhibits RB-1 through RB-13), executed Aug. 30, 2002.
Evidence-in-Support Statutory Declaration of Christopher Michael Ford (and supporting exhibits, Exhibits A and B), executed Sep. 6, 2002.
Evidence-in-Support Statutory Declaration of Ute Baumann (and supporting exhibits, Exhibits A and B), executed Sep. 11, 2002.
Evidence-in-Support Statutory Declaration of Margaret Anne Pallotta (and supporting exhibits, Exhibits A and B), executed Sep. 12, 2002.
U.S. Appl. No. 08/329,742, filed Oct. 26, 1994, Fry et al.
Baba et al., "Cultivation of rice protoplasts and their transformation mediated by Agrobacterium spheroplasts," Plant Cell Physiol, 27(3):463-471, 1986.

(Continued)

*Primary Examiner*—Cynthia Collins
(74) *Attorney, Agent, or Firm*—M. Todd Rands; Howrey LLP

(57) ABSTRACT

Disclosed are processes for producing stably transformed fertile wheat a system of transforming wheat via *Agrobacterium*. This invention provides methods transforming a variety of explants, such as freshly isolated or pre-cultured immature embryos, embryogenic callus and suspension cells. Also disclosed are methods for recovering transgenic plants after transformation within a short period of time, if the explants are regenerable at the time of transformation. Thus the frequency of somaclonal variation associated with prolonged in vitro culture period is significantly reduced. The transformation frequency using this system is comparable to or better than published methods using other systems, such as microprojectile bombardment.

10 Claims, 12 Drawing Sheets

OTHER PUBLICATIONS

Barcelo et al., "Transgenic cereal (tritordeum) plants obtained at high efficiency by microprojectile bombardment of inflorescence tissue," *Plant J*, 5(4):583-592, 1994.

Becker, Brettschneider and Lörz, "Fertile transgenic wheat from microprojectile bombardment of scutellar tissue," *Plant J.*, 5(2):299-307, 1994.

Boulton et al., "Specificity of Agrobacterium-mediated delivery of maize streak virus DNA to members of the Gramineae," *Plant Mol Biol*, 12:31-40, 1989.

Casas et al, "Transgenic sorghum plants via microprojectile bombardment," *Proc. Natl. Acad. Sci. USA*, 90:11212-11216, 1993.

Chan et al., "*Agrobacterium*-mediated production of transgenic rice plants expressing a chimeric α-amylase promoter /β-glucuronidase gene," *Plant Molecular Biology*, 22:491-506, 1993.

Cheng et al., "Efficient stable transformation of wheat suspension cells mediated by *Agrobacterium tumefaciens*," In- Vitro, 32(3 pt 2):105A, 1996.

Chibbar et al., "Transient expression of marker genes in immature zygotic embryos of spring wheat (*Triticum aestivum*) through microprojectile bombardment," *Genome*, 34:453-460, 1991.

Christou, Ford and Kofron, "Production of transgenic rice (*Oryza sativa* L.) plants from agronomically important Indica and Japonica varieties via electric discharge particle acceleration of exogenous DNA into immature zygotic embryos," *Biotech.*, 9:957-962, Oct. 1991.

Datta, Peterhans, Datta and Potrykus, "Genetically engineered fertile Indica-rice recovered from protoplasts," *Biotech.*, 8:736-740, Aug., 1990.

Dommisse et al., "Onion is a monocotyledonous host for *Agrobacterium*," *Plant Science*, 69:249-257, 1990.

Fromm, Morrish, Armstrong, Williams, Thomas and Klein, "Inheritance and expression of chimeric genes in the progeny of transgenic maize plants," *Biotech.*, 8:833-839, Sep. 1990.

Fromm, Taylor and Walbot, "Expression of genes transferred into monocot and dicot plant cells by electroporation," *Proc. Natl. Acad. Sci.* USA, 82:5824-5828, Sep. 1985.

Fromm, Taylor and Walbot, Stable transformation of maize after gene transfer by electroporation, *Nature*, 319(27): 791-793, Feb., 1986.

Golovkin et al., "Production of transgenic maize plants by direct DNA uptake into embryogenic protoplasts," *Plant Science*, 90:41-52, 1993.

Gordon-Kamm et al., "Transformation of Maize Using Microprojectile Bombardment: An Update and Perspective, " *In: Vitro Cell. Dev. Biol.*, 27P:21-27, Jan., 1991.

Gordon-Kamm, Spencer, Mangano, Adams, Daines, Start, O'Brien, Chambers, Adams, Jr., Willetts, Rice Mackey, Krueger, Kausch and Lemaux, "Transformation of maize cells and regeneration of fertile transgenic plants," *Plant Cell*, 2:603-618, Jul., 1990.

Gould, Devey, Hasegawa, Ulian, Peterson and Smith, "Transformation of *Zea mays* L. using *Agrobacterium tumefaciens* and the shoot apex," *Plant Physiol.*, 95:426-434, 199 1.

Graves and Goldman, ",*Agrobacterium tumefaciens*-mediated transformation of the monocot genus *Gladiolus*: Detection of expression of T-DNA-encoded genes," *J. Bacteriol*, 169(4):1745-1746, 1987.

Graves and Goldman, "The transformation of *Zea mays* seedlings with *Agrobacterium tumefaciens*," *Plant Molecular Biology*, 7:43-50, 1986.

Grimsley et al, "*Agrobacterium*-mediated delivery of infectious maize streak virus into maize plants," *Nature*, 325: 177-179, 1987.

Grimsley et al, "DNA transfer from *Agrobacterium* to *Zea mays* or *Brassica* by agroinfection is dependent on bacterial virulence functions," *Mol Gen. Genet.*, 217:309-316, 1989.

Grimsley et al, "Meristematic tissues of maize plants are most susceptible to agroinfection with maize streak virus," *Biotech.*, 6:185-189, 1988.

Hagio et al, "Production of fertile transgenic barley (*Hordeium vulgare* L.) plant using the hygromycin-resistance marker," *Plant Cell Reports*, 14:329-334, 1995.

Hayakawa, Zhu, Itoh, Kimura, Izawa, Shimamoto and Toriyama, "Genetically engineered rice resistant to rice stripe virus, an insect-transmitted virus," *Proc. Natl. Acad. Sci.* USA, 89:9865-9869, Oct., 1992.

Hess et al., "Transformation experiments by pipetting *Agrobacterium* into the spikelets of wheat (*Triticum aestivum* L.)," *Plant Science*, 72:233-244, 1990.

Hiei, Ohta, Komari and Kumashiro, "Efficient transformation of rice (*Oryza sativa* L.) mediated by *Agrobacterium* and sequence analysis of the boundaries of the T-DNA," Plant J., 6(2):271-282, 1994.

Hood et al., "Mediated Transformation of Wheat," Supplement to *Plant Physiology*, 105(1):607, May, 1994.

Hooykaas et al., "Expression of Ti plasmid genes in monocotyledonous plants infected with *Agrobacterium tumefaciens*," *Nature*, 311:763-764,1984.

International Search Report dated Feb. 4, 1998 (MOBT: 021P)(PCT/US97/10621).

Ishida, Saito, Ohta, Hiei, Komari and Kumashiro, "High efficiency transformation of maize (*Zea mays* L.) mediated by *Agrobacterium tumefaciens*," *Nature Biotech.*, 14:745-750, Jun., 1996.

Jähne et al., "Regeneration of transgenic, microspore-derived, fertile barley," *Theor. Appl. Genet.*, 89:525-533, 1994.

Jefferson, Assay chimeric genes in plants: The GUS gene fusion system, *Plant Mol. Biol. Rep.*, 5:387-405, 1987.

Jefferson, Kavanagh and Bevan, GUS fusions: β-glucuronidase as a sensitive and versatile gene fusion marker in higher plants, EMBO J., 6(13):3901-3907, 1987.

Knutzon et al., "Modification of *Brassica* seed oil by antisense expression of a steraroyl-acyl carrier protein desaturase gene," *Pro. Natl. Acad. Sci. USA*, 89:2624-2628, Apr., 1992.

Kornienko et al., "Transformation of the wheat *Triticum aestivum* with a bonary vector system of *Agrobacterium* plasmids," *Commonwealth Agricultural Bureau Database*, DN-931642242 in *Pushchino Meeting Info.: 1 Vsesoyuznyi Simpozium Pushchino*, 20-22, Noyabrya, pp. 20-21, 128-129,1991.

Koziel et al, "Field performance of elite transgenic maize plants expressing an insecticidal protein derived from *Bacillus thuringiensis*," *Biotechnology*, I 1: 194-200, 1993.

Kramer et al., "Selection of transformed protoplast-derived *Zea mays* colonies with phosphinothricin and a novel assay using the pH indicator chlorophenol red," *Plants*, 190:454-458, 1993.

Langridge et al., "Transformation of cereals via, *Agrobacterium* and the pollen pathway: a critical assessment," *Plant J*, 2(4):631-638, 1992.

Liu et al, "Multiple copies of virG enhance the transient transformation of celery, carrot and rice tissues by, *Agrobacterium tumefaciens*," *Plant Mol. Biol.*, 20.1071-1087, 1992.

Lowe et al., "Germline transformation of maize following manipulation of chimeric shoot meristems," *Biotech.*, 13:677-682, 1995.

Luo and Wu, A simple method for the transformation of rice via the pollen-tube pathway, *Plant Mol. Biol. Rep.*, 6:165-174, 1988.

Mahalakshmi and Khurana, *Agrobacterium*-mediated gene delivery in various tissues and genotypes of wheat (*Triticum aestivum* L.), *J Plant Biochem. Biotech.*, 4:55-59, 1995.

Miller, *In: Experiments in Molecular Genetics*, Cold Spring Harbor Laboratory, Cold Spring Harbor, New York, 1972.

Mooney and Goodwin, Adherence of *Agrobacterium tumefaciens* to the cells of immature wheat embryos, *Plant Cell, Tissue and Organ Culture*, 25:199-208, 1991.

Mooney, Goodwin, Demiis and Llewellyn, *Agrobacterium tumefaciens*-gene transfer into wheat tissues, *Plant Cell, Tissue and Organ Culture*, 25:209-218, 1991.

Nehra et al, "Wheat transformation: methods and prospects, " *Plant Breeding, Abstracts*, 65(6):803-808, 1995.

Nehra, Chibbar, Leung, Caswell, Mallard, Steinhauer, Baga and Kartha, "Self-fertile transgenic wheat plants regenerated from isolated scutellar tissues following microprojectile bombardment with two distinct gene constructs," *Plant J.*, 5(2):285-297, 1994.

Omirulleh et al., "Activity of a chimeric promoter with the doubled CaMV 35S enhancer element in protoplast-derived cells and transgenic plants in maize," *Plant Mol. Biol.*, 21:415-428, 1993.

Paszkowski, Pisan, Shillito, Hohn, Hohn and Potrykus, "Genetic transformation of *Brassica compestris var. rapa* protoplasts with an engineered cauliflower mosaic virus genome," *Plant Mol. Biol.*, 6:303-312, 1986.

Paszkowski, Shillito, Saul, Manddk, Hohn, Hohn and Potrykus, Direct gene transfer to plants, *EMBO J.*, 3(12):2717-2722,1984.

Peña et al., "Transgenic rye plants obtained by injecting DNA into young floral tillers," *Letters to Nature*, 325:274-276, Jan. 15, 1987.

Peña, Lörz and Schell, "Transgenic rye plants obtained by injecting DNA into young floral tillers," *Nature*, 325(15), 274-276, Jan., 1987.

Perl et al, "Improvement of plant regeneration and GUS expression in scutellar wheat calli by optimization of culture conditions and DNA-microprojectile delivery procedures," *Mol. Gen. Genet.*, 235:279-284, 1992.

Picard, Jacquemin, Granier, Bobin and Forgeois, Genetic transformation of wheat (*Triticum aestivum*) by plasmid DNA uptake during pollen tube germination, *In:* VIIth International Wheat Genetics Symposium, Cambridge, The University of Cambridge, 779-781, 1988.

Poirier et al., "Polyhydroxybutyrate, a Biodegradable Thermoplastic, Produced in Transgenic Plants," *Science*, 256:520-523, Apr. 24, 1992.

Potrykus et al., "Direct gene transfer to cells of a graminaceous monocot," *Mol. Gen. Genet.*, 199:183-188, 1985.

Pukhal'skii et al., "Genetic transformation of wheat (*Triticum aestivum* L.) by *Agrobacterium tumefaciens,*" *Biological Abstracts Database*, DN-99448911 in *Genetika*, 32(11):1596-1600.

Raineri, Bottino, Gordon and Nester, *Agrobacterium*-mediated transformation of rice (*Oryza saliva* L.), Biotech., 8:33-38, Jan., 1990.

Rhodes, "Corn: from protoplasts to fertile plants," *Biotech.*, 7:548, 1989.

Rhodes, Pierce, Mettler, Mascarenhas and Detmer, Genetically transformed maize plants from protoplasts, *Science*, 240:204-207, Apr., 1988.

Sambrook, Fritsch and Maniatis, *In: Molecular Cloning: A Laboratory Manual*, 2nd Ed., Cold Spring Harbor Laboratory Press, 1989.

Sanford, "Biolistic plant transformation," *Physiologia Planarum*, 79:206-209, 1990.

Sanford, "The biolistic process," *Tibtech*, 6:299-302, Dec., 1988.

Sautter, Waldner, Neuhaus-Url, Galli, Neuhaus and Potrykus, "Micro-targeting: High efficieny gene transfer using a novel approach for the acceleration of mircoprojectiles," *Biotech.*, 9:1080-1085, Nov., 1991.

Schläppi and Hohn, "Competence of immature maize embryos for *Agrobacterium*-mediated gene transfer," *Plant Cell*, 4:7-16, 1992.

Shillito, Saul, Paszkowski, Müller and Potrykus, "High efficiency direct gene transfer to plants," *Biotech.*, 3:1099-1103, Dec., 1985.

Shimamoto et al, "Fertile transgenic rice plants regenerated from transformed protoplasts," *Nature*, 338:274-276, 1989.

Smith and Hood, "*Agrobacterium tumefaciens* transformation of monocotyledons," *Crop Science*, 35(2):301-309, 1995.

Somers, Rines, Gu, Kaeppler and Bushnell, Fertile, transgenic oat plants, *Biotech.*, 10: 1589-1594, Dec., 1992.

Southern, "Detection of specific sequences among DNA fragments separated by gel electrophoresis," *J. Mol. Biol.*, 98:503-517,1975.

Spencer et al., "Segregation of transgenes in maize," *Plant Mol. Biol*, 18:201-210, 1992.

Töpfer, Gronenborn, Schell and Steinbiss, Uptake and transient expression of chimeric genes in seed-derived embryos, *Plant Cell*, 1: 133-139, Jan., 1989.

Vasil, Castillo, Fromm and Vasil, "Herbicide resistant fertile transgenic wheat plants obtained by microprojectile bombardment of regenerable embryogenic callus," *Biotech.*, 10:667-674, Jun., 1992.

Vasil, Srivastava, Castillo, Fromm and Vasil, "Rapid production of transgenic wheat plants by direct bombardment of cultured immature embryos," *Biotech.*, 11:1553-1558, Dec., 1993.

Vijayachandra et al., "Rice scutellum induces *Agrobacterium tumefaciens* vir genes and T-strand generation," *Plant Molecular Biology*, 29:125-133, 1995.

Walters et al., "Transformation and inheritance of a hygromycin phosphotransferase gene in maize plants," *Plant Mol. Biol.*, 18:189-200, 1992.

Wan and Lemaux, "Generation of large numbers of independently transformed fertile barley plants," *Plant Physiol.*, 104:37-48, 1994.

Wang et al., "Transient expression of foreign genes in rice, wheat and soybean cells following particle bombardment," *Plant Molecular Biology*, 11:433-439, 1988.

Wan-Yin et al., "*Agrobacterium tumefaciens* can transform *Triticum aestivum* and *Hordeum vulgare* of gramineae," *Science in China (Series B)*, 33(1):27-33, 1990.

Weeks, Anderson and Blechl, Rapid production of multiple independent lines of fertile transgenic wheat (*Triticum aestivum*), Plant Physiol., 102:1077-1084, 1993.

Wilmink et al, Expression of the GUS-gene in the monocot tulip after introduction by particle bombardment and *Agrobacterium*, Plant Cell Reports, 11:76-80, 1992.

Zaghmout, Transformation of protoplasts and intact cells from slowly growing embryogenic callus of wheat (*Triticum aestivum* L.), Theor. Appl. Genet., 89:577-582, 1994.

Zhou et al, "Stably transformed callus of wheat by electroporation-induced direct gene transfer," *Plant Cell Reports*, 12:612-616, 1993.

Zhou et al., "Functional properties of ficoll and their influence on anther culture responses of wheat," *Plant Cell, Tissue and Organ Culture*, 30:77-83, 1992.

Zhou, Arrowsmiffi, Fromm, Hironaka, Taylor, Rodriguez, Pajeau, Brown, Santino and Fry, "Glyphosate- tolerant CP4 and GOX genes as a selectable marker in wheat transformation," *Plant Cell Reports*, 15:159-163, 1995.

Dale, P.J., et al., (1989), *Plant Science*,63:237-245—"Agroinfection of wheat: inoculation of in vitro grown seedlings and embryos".

Deng, W-Y., et al. (1990), *Science in China*, Series B 33:27-34—"*Agrobacterium tumefaciens* can transform *Triticum aestivum* and *Hordeum vulgare* of gramineae".

Viertel, K. and Hess, D (1996), *Plant Cell, Tissue and Organ Culture*, 44:183-188—"Shoot tips of wheat as an alternative source for regenerable embryogenic callus cultures".

Zaghmout, O.M.-F. (1994), *Theor. Appl. Genet.* 89:577-582—"Transformation of protoplasts. and intact cells from slowly growing embryogenic callus of wheat (*Triticum aestivum* L.)".

Deng, W.Y, et al., (1988) *Genetic Manipulation in Crops Newsletter*, 4:1-2—"Transformation of some ceral crops with *Agrobacterium tumefaciens*".

Zilberstein, A., et al., (1994), 4th International Congress of Plant Molecular Biology, Abstract No. 2013.

Dong, J., (1996) *Molecular Breeding*, 2:267-276—"*Agrobacterium*-mediated transformation of Javanica rice".

Rashid, H., et al., (1996), *Plant Cell Reports*, 15:727-730—"Transgenic plant production mediated by *Agrobacterium* in *Indica* rice".

Li, X-Q., et al., (1992), *Plant Molecular Biology*, 20:1037-1048—"Factors influencing *Agrobacterium*-mediated transient expression of *gusA* in rice".

Chan, M-T, et al., (1992), *Plant Cell Pysiol.*, 33(5):577-583—"Transformation of Indica Rice (*Oryza sativa* L.) mediated by *Agrobacterium tumefaciens*".

Creissen, G., et al., (1990), *Plant Cell Reports*, 8:680-683—"*Agrobacterium*—and microprojectile-mediated viral DNA delivery into barley microspore-derived cultures".

Ritchie, S.W. et al., (1993), Transgenic Research, 2:252-265—"*Agrobacterium tumefaciens*-mediated expression of *gusA* in maize tissues".

Shen, W-H., et al., (1993), *Proc. Natl. Acad. Sci. USA*, 90:1488-1492—"T-DNA transfer to maize cells: Histochemical investigation of β-glucoronidase activity in maize tissues".

Park, S.H. and Smith, R.H., (1993), In vitro 29A:P1102 (abstract)—"Selection of maize transformants from shoot apex cultures cocultivated with *Agrobacterium* containing the bar gene".

Tingay, S. et al., (1997), *The Plant Journal*, 11(6):1369-1376 "*Agrobacterium tumefaciens*-mediated barley transformation".

He, D.G., et al., (1994), *Plant Cell Reports*, 14:192-196—"Transformation of wheat (*Triticum aestivum* L.) through electroporation of protoplasts".

Brettell, R.I.S. and Murray, F.R., (1995), *Biotechnology and Genetic Engineering Reviews*, 13:315-334—"DNA Transfer and Gene Expression in Transgenic Cerals".

Statement of Grounds and Particulars in Support of Opposition in relation to Australian Application No. 738153 (34028/97) In the name of Monsanto Company (Opposition filed in Australian counterpart of the instant application).

O.D. Anderson, "Transgenic Wheat-Challenges and Opportunities," *Transgenic Cereals*, pp. 1-27 (2000).

R.J. Henry, "Molecular Distinction Between Monocotyledons and Dicotyledons: More Than a Simple Dichotomy," *Plant Molecular Biology Reporter*, 15:216-218 (1997).

R. Birch, "Plant Transformation: Problems and Strategies for Practical Application," *Annual Review of Plant Physiology and Plant Molecular Biology*, 48:297-326 (1997).

M. Abedinia, "An Efficient Transformation System for the Australian Rice Cultivar, Jarrah," *Australian Journal of Plant Physiology*, 24:133-141 (1997).

R.I.S. Brettell, Assessment of Methods for the Genetic Transformation of Wheat, *Improvement of Cereal Quality by Genetic Engineering*, pp. 3-9 (1994).

F. Morrish, "Microprojectile Bombardment: A Method for the Production of Transgenic Cereal Crop Plants and Functional Analysis of Genes," *Transgenic Plants Fundamentals and Applications*, pp. 133-171 (1993).

\* cited by examiner

PROTOCOL 1

TRANSFORMATION OF IMMATURE EMBRYOS

IMMATURE EMBRYOS

↓

Inoculation with *Agrobacterium*

1-3 h ↓

CO-CULTURE 2-3 d ↓

DELAY OF SELECTION 2-5 d ↓

CALLUS INDUCTION
SELECTION 2 w ↓ Selective agent

REGENERATION 1

2 w ↓ Selective agent

REGENERATION 2

2-3 w ↓ Selective agent

PLANT FURTHER GROWTH 2-4 w ↓ Selective agent

SOIL

FIG. 11

PROTOCOL 2

SUSPENSION CELL TRANSFORMATION

WHEAT CV. MUSTANG

SUSPENSION CELLS

Subculture 1-3d  ↓

INOCULATION WITH *AGROBACTERIUM*

30 min-3 h   ↓

CO-CULTURE 2-3 d   ↓

DELAY OF SELECTION 1-3 d   ↓

SELECTION 40-60 d   ↓   Selective agent

TRANSFORMED COLONIES

FIG. 12

METHODS FOR THE PRODUCTION OF STABLY-TRANSFORMED, FERTILE WHEAT EMPLOYING AGROBACTERIUM-MEDIATED TRANSFORMATION AND COMPOSITIONS DERIVED THEREFROM

This is a continuation of application Ser. No. 09/234,974, filed Jan. 21, 1999, now abandoned, which is a continuation of application Ser. No. 08/667,188, filed Jun. 21, 1996, now abandoned, the entire contents of each of which is herein incorporated by reference.

1. BACKGROUND OF THE INVENTION 1.1 Field of the Invention

The present invention relates to the field of molecular biology. More specifically, it concerns methods for the incorporation of foreign DNA into the genome of monocotyledonous plants, and in particular, wheat. Provided herein are reproducible systems for genetically transforming wheat, methods of selecting stable genetic transformants from suspensions of transformed cells, and methods of producing fertile plants from the transformed cells. Exemplary methods include the use of *Agrobacterium*-mediated transformation to introduce nucleic acids into cells, and selectable and/or screenable marker systems, for example, genes which confer resistance (e.g., antibiotic, herbicide, etc.), or which contain an otherwise phenotypically observable trait. In other aspects, the invention relates to the production of stably transformed and fertile wheat plants, gametes and offspring from these plants.

1.2 Description of the Related Art

The entire text of U.S. patent application Ser. No. 08/329,742 filed Oct. 26, 1994 is hereby incorporated by reference in its entirety. During the past decade, it has become possible to transfer genes from a wide range of organisms to crop plants by recombinant DNA technology. This advance has provided enormous opportunities to improve plant resistance to pests, diseases and herbicides, and to modify biosynthetic processes to change the quality of plant products (Knutson et al., 1992; Piorer et al., 1992; Vasil et al., 1992). However, the availability of an efficient transformation method to introduce foreign DNA has been a substantial barrier for most monocot species, including maize, rice, oat, barley, and particularly wheat.

1.2.1 Available Methods for Transforming Monocotyledonous Plants

There have been many methods attempted for the transformation of monocotyledonous plants but only a few methods have resulted in stable transformation. Two methods are currently employed for most transgenic studies in monocot species: direct DNA transfer into isolated protoplasts and microprojectile-mediated DNA delivery (Shimamoto et al., 1989; Fromm et al., 1990). More recently, additional methods have also been developed for use in monocots. Following is a brief description of the methods that have resulted in stably transformed and fertile monocots capable of transferring genes to their progeny in a Mendelian fashion.

1.2.1.1 Biolistics

"Biolistics" is most widely used transformation method for monocotyledons. In the "biolistics" method microprojectile particles are coated with DNA and accelerated by a mechanical device to a speed high enough to penetrate the plant cell wall and nucleus (Intl. Pat. Appl. Publ. No. WO 91/02071). The foreign DNA gets incorporated into the host DNA and results in a transformed cell. There are many variations on the "biolistics" method (Sanford, 1990; Fromm et al., 1990; Christou et al., 1988; Sautter et al., 1991). This method has been successfully used to produce stably transformed monocotyledonous plants including rice, maize, wheat, barley, and oats (Christou et al., 1991; Gordon-Kamm et al., 1990; Vasil et al., 1992, 1993; Wan et al., 1993; Sommers et al., 1992).

The microprojectile-mediated DNA delivery method may use immature embryos or immature embryo derived calli as target tissues. Transgenic plants have been recovered from the microprojectile bombardment method in maize, oat, barley and wheat (Gordon-Kamm et al., 1990; Somers et al., 1992; Wan et al., 1994; Vasil et al., 1992).

The microprojectile bombardment method generally takes 10 to 15 months to obtain transgenic plants (Gordon-Kamm et al., 1990; Vasil et al., 1992). Even with the more recent improvements in transformation methods using immature embryos as target tissues, it still requires 4 to 6 months to recover transgenic plants (Weeks et al., 1993; Vasil et al., 1992; 1993; Becker et al., 1994). The transformation frequency by these methods is variable ranging from about one event from 100 to 1000 bombarded embryos.

1.2.1.2 Electroporation

The protoplast methods have been widely used in rice, where DNA is delivered to the protoplasts through liposomes, PEG, and electroporation. While a large number of transgenic plants have been recovered in several laboratories (Shimamoto et al., 1989; Datta et al., 1990), the protoplast methods require the establishment of long-term embryogenic suspension cultures. Some regenerants from protoplasts are infertile and phenotypically abnormal due to the long-term suspension culture (Davey et al., 1991; Rhodes et al., 1988). These procedures have been especially useful for rice and some grasses.

Transformation by electroporation involves the application of short, high voltage electric fields to create "pores" in the cell membrane through which DNA is taken-up. This method has been used to produce stably transformed monocotyledon plants, (Pasazkowski et al., 1985; Shillito et al., 1985; Fromm et al., 1986) especially from rice (Shimamoto et al., 1992; Datta et al., 1990, 1992; Hayakawa et al., 1992).

1.2.1.3 Chemical Treatment of Protoplasts

The polyethylene glycol (PEG) method is simply a chemical treatment in the presence of the protoplasts and the DNA (Shillito et al., 1985; Rhodes et al., 1988). The PEG facilitate the uptake of the DNA.

1.2.1.4 Other Methods

A number of other methods have been reported for the transformation of monocotyledon plants. The methods reported to produce fertile transgenic monocotyledon plants include the "pollen tube method" (Intl. Pat. Appl. Publ. No. WO 93/18168; Zahir, 1993, Luo and Wu, 1988) and macroinjection of DNA into floral tillers (Du et al., 1989; Picard et al., 1988; De la Pena et al., 1987) and tissue incubation of seeds in DNA solutions (Tofer et al., 1989). Direct injection of exogenous DNA into the endosperm of a fertilized plant ovule at the onset of embryogenesis was disclosed in Intl. Pat. Appl. Publ. No. WO 94/00583. Besides the protoplast and the biolistics methods of transformation other methods are not reproducible or predictable. There is usually evidence of expression but seldom is the DNA transmitted to the progeny.

1.3 Deficiencies in the Prior Art

The one important area where there has been little significant progress in the art has been the adaptation of bacterial-mediated methods of transformation in monocots. While widely useful in dicotyledonous plants, *Agrobacterium*-mediated gene transfer has been disappointing when adapted to use in monocots. There are several reports in the literature claiming *Agrobacterium* transformation of monocotyledons which are discussed in Intl. Pat. Appl. Publ. No. WO 94/0077. These are specifically the methods of Gould et al., 1991; Mooney et al., 1991; and Raineri et al., 1990, which claim *Agrobacterium* transformation of maize, rice and wheat. There is some evidence of gene transfer in these methods but they lack convincing evidence for transfer efficiency, reproducibility, and confirmation of gene transfer (Potrykus, 1990), and lack of transfer to the progeny when plants are produced. In the work of Gould where evidence of transformed plants was presented there was no Mendelian inheritance of the genes.

De LaFonteyne et al. (Intl. Pat. Appl. Publ. No. WO 92/06205) described a process for the transformation of maize cells using *A. tumefaciens* strains in combination with a transposon-mediated integration method, but the success of such methods in other species was not demonstrated.

Mooney et al. (1991) produced transformed cells from wheat embryos co-cultivated with *A. tumefaciens* but the frequency of transformation was very low and often unreproducible. Chan et al. (1993) subsequently attempted to produce transgenic rice plants using *A. tumefaciens*, but their methods have not been widely accepted owing to a lack of sufficient molecular and genetic evidence of transgenic plant production.

More recent attempts by Hiei et al, (1994) suggested that transgenic rice plants could be obtained following *A. tumefaciens* transformation, but that the particular bacterial strains used and the choice of bacterial vectors were critical for successfully obtaining transgenes. A recent paper by Ishida et al. (1996) indicated a high-efficiency transformation of maize was possible by co-culture of immature embryos with *A. tumefaciens*. In both reports on rice and the maize transformation, a super binary vector pTOK233 containing the virb, virC and virG genes was used to achieve high-efficiency transformation. A recent report by Saito et al. (Intl. Pat. Appl. Publ. No. WO 95/06722) discloses a method of transforming monocotyledons using scutellum of non-dedifferentiated immature embryos using *A. tumefaciens*.

Despite the fact that wheat is the most widely-grown cereal crop in the world, unfortunately no convincing reports exist on the use of *Agrobacterium* transformation methods in the preparation of stable, fertile wheat transgenic plants. Likewise, no methods have been developed using immature embryonic or callus tissues for stable, high-frequency transformation of wheat. Therefore, what is lacking in the prior art is an *Agrobacterium*-mediated method for preparing fertile, transgenic wheat plants.

2. SUMMARY OF THE INVENTION

The present invention seeks to overcome these and other inherent deficiencies in the prior art by providing novel processes for the stable transformation of monocotyledonous plants, and in particular, wheat, using *Agrobacterium*-mediated methods.

It is therefore a particular object of the present invention to provide techniques that will allow one to prepare transgenic, fertile wheat which are preferably diploid and which have been stably transformed through the introduction of one or more desired genes into the genome of these species.

The present invention thus relates generally to methods for the production of transgenic wheat plants. As used herein, the term transgenic plants is intended to refer to plants that have incorporated exogenous genes or DNA sequences, including but not limited to genes or DNA sequences which are perhaps not normally present, genes not normally transcribed and translated ("expressed") in a given cell type, or any other genes or DNA sequences which one desires to introduce into the non-transformed plant, such as genes which may normally be present in the non-transformed plant but which one desires to have altered expression.

The present invention can be used with any plant species. It is particularly useful for monocot species. More particularly, it is useful in plant species which cannot remain in a callus state for long periods of time without losing the ability to regenerate. One particularly useful species in the present invention is wheat. Preferred species include *Triticum aestivum, T. turgidum* and *T. monococum* wheat, with *T. aestivum* being particularly preferred. The present invention, when applied to wheat, has the advantage of being genotype independent. That is, it can be used with any type of wheat variety, including both winter and spring wheat. It can be used to produce transgenic wheat plants from spring cultivars, such as, for example, Bobwhite and Marshall PAVOT1, UC702, and Panewawa as well as winter cultivars, such as, for example, HY368, Neeley, FL302, RH91, R332, R1269 and R585.

The present invention is used to introduce foreign DNA into regenerable plant tissue. Any type of foreign DNA can be inserted into the plant species using the method of the present invention. Generally, "foreign DNA" can be defined to include any type of DNA which is inserted into a plant cell from outside the plant cell. Methods for inserting cloned DNA into suitable plasmid constructs, and manipulation of appropriate *Agrobacterium* delivery strains are generally well known.

The type of DNA included in the foreign DNA can include DNA which already is present in the plant cell, DNA from another plant, DNA from a different organism, or a DNA generated externally, such as a DNA sequence containing an anti-sense message of a plant gene, or a DNA sequence encoding a synthetic version of a gene where the nucleotide sequence has been modified.

In a preferred embodiment, *Agrobacterium tumefaciens* C58, anopaline strain is used to mediate the transfer of DNA into a wheat cell. Other preferred strains for use in the practice of the invention include octopine strains, LBA4404 or agro pine strains, e.g., EHA101 or EHA105.

In preferred embodiments, the foreign DNA contains a DNA sequence which can function in a regenerable plant tissue as a selection device. Such DNA can include a gene which would function in a regenerable plant tissue to produce a compound which would confer upon the plant tissue resistance to an otherwise toxic compound. These genes are well known in the art and can confer resistance to compounds such as antibiotics like kanamycin (Dekeyser et al., 1989), and herbicides like glyphosate (Della-Cioppa et al., 1987 and bialaphos (Vasil et al., 1992). Other selection devices can be used within the scope of the present invention. Such genes include those for CP4, BAR, hygromycin, phosphotransferase (NPT) and dihydrofolate reductase (dhfr).

In one embodiment, a method is disclosed for producing a transgenic wheat plant. The method involves in a general sense, establishing a culture from a wheat plant to be transformed, transforming the culture with an *Agrobacterium* comprising a DNA composition that includes a genetic component one desires to introduce into the wheat genome, identifying or selecting a transformed cell line, and regenerating a transgenic wheat plant therefrom.

In another important embodiment, the invention provides a method for producing a fertile transgenic wheat plant. The process involves establishing a regenerable culture from a wheat plant to be transformed, introducing a DNA composition comprising a genetic component one desires to introduce into the genome of said wheat plant, by *Agrobacterium* transformation, identifying or selecting a transformed cell line; and regenerating a fertile transgenic wheat plant from the transformed cell line. The DNA is transmitted through a complete sexual cycle of the transgenic plant to its progeny, and the progeny contain a stable, chromosomally-integrated copy of the selectable or screenable marker gene which was transformed into the parent via *Agrobacterium* transformation.

In these embodiments, the DNA composition comprises a plasmid, and particularly a recombinant plasmid such as pMON18365 which contains an nptII gene. Other genes of interest include selectable or screenable marker genes such as e.g., any of those described herein, including GUS, green fluorescent protein (GFP), luciferase (LUX), CP4 and nptII genes Examples of transposons and associated antibiotic resistance genes include the transposons Tns (bla), Tn5 (nptII), Tn7 (dhfr), penicillins, kanamycin (and neomycin, G418, bleomycin); methotrexate (and trimethoprim); chloramphenicol; kanamycin and tetracycline.

Characteristics useful for selectable markers in plants have been outlined in a report on the use of microorganisms (Advisory Committee on Novel Foods and Processes, July 1994). These include i) stringent selection with minimum number of nontransformed tissues; ii) large numbers of independent transformation events with no significant interference with the regeneration; iii) application to a large number of species; and iv) availability of an assay to score the tissues for presence of the marker. As mentioned, several antibiotic resistance markers satisfy these criteria, including those resistant to kanamycin (nptII) hygromycin B (aphIV) and gentamicin (aacC3 and aacC4). A more complete description and list is included in Table 1.

TABLE 1

| Type | Examples |
|---|---|
| Aminoglycoside antibiotics | |
| 1) phosphotransferase enzymes (APH) | APH (3')II |
| | APHIV |
| 2) adenyltransferase enzymes (AAD) | ADD (3") |
| 3) acetyltransferases (AAC) | AAC(3)-I |
| | AAC(3)-III |
| | AAC(3)-IV |
| Chloramphenicol | |
| chloramphenicol acetyl transferase (CAT) | |
| β-Lactam antibiotics | TEM-1-β-lactamase |
| β-lactamase | |
| 2,4-Diaminopteridones dihydrofolate reductase | |
| Glycopeptides | TN5-bleomycin |
| Pyridone carboxylic acids | nalidixic acid resistance |
| DNA gyrase | |
| Rifamycins | rifamycin resistance |
| resistant RNA polymerase | |
| Macrolides | erythromycin resistance |
| 50S subunit methylation | |

TABLE 1-continued

| Type | Examples |
|---|---|
| Tetracyclines | excretes antibiotic from |
| bind to S4 and S18 proteins of 70S ribosome subunit | cell |

Alternatives to antibiotic resistance markers have been developed for plants (Advisory Committee on Novel Foods and Processes, July 1994). These include metal tolerance markers, completation systems with auxotrophic markers, sugar catabolism markers, L-canavanine resistance markers and markers for resistance to lysine and threonine and S-aminoethyl L-cysteine. Examples and additional description are shown in Table 2.

TABLE 2

| Marker | Example |
|---|---|
| Herbicide resistance | herbicide resistance can be used as a selectable marker in plants e.g., tolerance to glyphosate and bromoynil |
| Metal tolerance | metal tolerance, through insertion of a mammalian metallothionein gene |
| Resistance to lysine and threonine and to s-aminoethyl L-cysteine | two of the enzymes of the aspartate family biosynthetic pathway, which is regulated by several feedback inhibition loops, have been developed as selectable markers; asparatate kinase (AK) activity is inhibited by millimolar concentrations of lysine and threonine (LT); dihydrodipicoline synthase (DHPS) activity is inhibited by lysine and leads to sensitivity to the toxic lysine analogue, S-aminoethyl L-cysteine (AEC); transgeneic plants containing *E. coli* genes for expression of AK and DHPS can be grown on media containing LT and AEC respectively. |

Scorable markers may also be used in plants as alternatives to antibiotic resistance markers. Such markers are used to detect the presence or to measure the level of expression of the transferred gene. The use of scorable markers in plants to identify or tag genetically modified cells works well only when efficiency of modification of the cell is high. Some of the more commonly employed scorable markers include beta-glucuronidase (GUS), whose expression is detected by a blue color on incubation of the tissue with 5-bromo-4-chloro-3-indolyl-1-glucuronide; bacterial luciferase (LUX) whose expression is detected by light emission; firefly luciferase (LUC) whose expression is detected by light emission after incubation with luciferin; and β-galactosidase whose expression is detected by a bright blue color after the tissue is stained with 5-bromo-4-chloro-3-indolyl-β-D-galactopyranoside.

Preferred cells for practice of these methods include immature embryos, callus tissues, or suspension cells, and a preferred *Agrobacterium* species for transformation is *A. tumefaciens*, with strains such as C58 LBA4404 and EHA101 being particularly preferred.

The embryos to be transformed may either be freshly isolated from an immature caryopsis or isolated from an immature caryopsis and then pre-treated. The isolation of the immature embryo from the immature caryopsis may occur on the same day of inoculation, or alternatively, one, two, five, or even more days prior to inoculation. Likewise, the callus tissue may be isolated from an immature embryo or from non-embryonic plant cells. The embryo may be injured prior to transformation. The embryo or caryopsis may be one that is 2 or more days after anthesis, and when suspension cells are used, they may be cultures of individual cells or, alternatively, cell clusters.

The DNA to be transformed is preferably a recombinant plasmid, as described herein, and may comprise one or more promoters and/or 3' and/or 5' regions operatively linked to the particular genetic components to be transformed. Promoters such as CaMV 35S FMV, ubiquitin, rice actin or enhanced CaMV 35S promoters are particularly preferred.

When desirable, the plants derived from the transformation may be grown and progeny obtained. These progeny may be used to prepare transgenic seeds, or alternatively, bred with a second transgenic wheat plant to prepare a fertile, transgenic wheat plant that comprises one or more transgenes of interest. The seeds obtained from such progeny may be germinated, cultivated, and used to prepare subsequent generations of transgenic offspring which comprise the transgene originally transformed in the parental line.

In one embodiment of the present invention, an immature embryo from a plant is used as a starting material. Immature embryos can be produced using known method described in the art. For instance, the production of wheat immature embryos is described by Weeks et al. (1993) and Vasil et al. (1993).

In another preferred embodiment of the present invention, the regenerable plant tissues are calli. The preferred calli are embryogenic calli. Embryogenic calli are produced from immature embryos. These calli can be produced by isolating and culturing immature embryos on a nutrient media with carbohydrate and plant growth regulators. In the preferred embodiment of the present invention, when producing embryogenic calli from wheat, the elimination of embryo axis as described by Nehra et al., (1994) is not necessary.

Callus-producing medium are well known in the art and any culture medium or preparation method can be used. In the preferred embodiment, where wheat calli are prepared, a wheat immature embryo is cultured for 1 day up to one month, preferably for 4 to 7 days, on a modified MS medium comprising about 40 g/l maltose and about 2 mg/l 2,4-D. In another embodiment, the 2,4-D can be replaced by a combination of 0.5 mg/l 2,4-D and 2.2 mg/l pichloram (Chemservice). The medium is solidified by 2 g/l Gelrite® (Sigma Chemical, St. Louis, Mo.) or 4 g/l low-melting agarose.

After transformation, the regenerable plant tissue is placed in a medium capable of producing shoots from the regenerable tissue where the medium further contains a compound used to select regenerable tissue containing the selectable DNA sequences. This is in contrast to the prior art where regenerable plant tissue is generally subjected first to an extended period of selection prior to exposure of the regenerable tissue to a medium capable for producing shoots.

The medium used in this step can be any medium which permits the formation of shoots from the regenerable tissue. In one embodiment, a shoot-producing compound is added to the medium. These shoot-producing compounds are well known in the art (Mursahige and Skoog, 1962; Kasha et al., 1990). Such compounds include weak plant growth regulators and include IAA, IBA, and BA at low concentrations (Becker et al., 1994; Vasil et al., 1992). In another embodiment of the invention, a medium free of a plant growth regulator can be used to induce shoot formation (Weeks et al., 1993).

In a preferred embodiment, where an embryogenic wheat callus is to be regenerated, the medium comprises a modified MS medium with 0.2 mg/l 2,4-D (Murashige and Skoog, 1962; Wan and Lemaux, 1994).

The regenerable plant tissue is generally placed in this medium as quickly as possible in the present invention after transformation. Generally, this can range from about 1 day to about three weeks, but preferably from about 1 day to about two weeks, more preferably from about two to about three weeks. Most preferably the tissue is transferred to this medium from about one week to about two weeks after transformation. In most instance, the transfer will occur between about 5 and about 11 days.

The compound used to select regenerable tissue containing the selectable DNA sequences can be any of a variety of well known selection compounds, such as antibiotics and herbicides. Preferred compounds can include geneticin (G-418) (aminoglycoside) (Nehra et al., 1994), glyphosate (Della-Cioppa et al. 1987) and bialaphos (Vasil et al., 1992; Weeks et al., 1993).

The availability of alternative selection agents is an important requirement for commercial application of agriculture biotechnology. The use of kanamycin has been less successful for cereal crops because of the high endogenous level of tolerance (Dekeyser et al., 1989). Bialaphos has been widely used as a selection agent in cereal crop transformation (Weeks et al., 1993; Vasil et al., 1993; Becker et al., 1994; Nehra et al., 1994; Wan and Lemaux, 1994). However, it could potentially be a disaster to exclusively use genes encoding bialaphos resistance as a selectable marker in all transformation studies Other selectable markers are needed and the results demonstrate that the herein described rapid regeneration system works well with different selection agents.

After shoots have formed the shoots are transferred to a second medium capable of producing roots form said shoots. This medium can further contain a compound used to select regenerable tissue containing the selectable DNA sequences. Transfer to this medium occurs when sufficient shoots have developed, a generally known in the art. This occurs, for wheat, within 25 to 40 days after transformation.

The medium capable of producing roots can be any roof producing medium. These mediums are well known in the art (Weeks et al., 1993; Vasil et al., 1992). One preferred root-producing medium is a modified MS medium without any plant growth regulator (Murashige and Skoog, 1962; Zhou et al., 1992).

Once roots have been formed, the plants can then be transferred to soil and grown following methods known in the art to produce seeds.

The present invention discloses a reproducible efficient *Agrobacterium* method for transforming monocotyledons, especially wheat and corn with a conventional binary vector commonly used for transformation of dicotyledons. The invention provides a rapid and efficient *Agrobacterium* transformation and regeneration system, especially useful for the transformation of wheat and corn. Plants regenerated from this system are phenotypically normal and fully fertile. The transgenes are transmitted to R1 progeny in a Mendelian fashion.

In a preferred embodiment, the present invention provides a rapid and efficient transformation system for wheat using freshly isolated immature embryos, pre-cultured embryos and proliferated calli from immature embryos. The new transformation system takes about three months to obtain transgenic plants, and transformation frequencies with the novel methods disclosed herein are reproducibly 0.3 to 4.3%.

In a general sense, the present invention provides a method for producing a transformed monocotyledonous plant which contains exogenous DNA. Such a method generally involves isolating regenerable tissue from the plant, transferring into the regenerable tissue the foreign DNA by a 1 to 3 hour inoculation of the regenerable tissue with the *Agrobacterium* and co-culture of the plant tissue with the *Agrobacterium* for 2–3 days. Typically the foreign DNA to be inserted into the plant genome comprises a selectable marker DNA sequence, where the sequence can function in a regenerable tissue as a selection device: The cells are then grown from between about 2 day to about 5 days on callus medium containing antibiotics to kill the *Agrobacterium*, and approximately 1 to 2 weeks later, the regenerable tissue is placed in a medium capable of producing shoots from the tissue. This medium further contains a compound used to select regenerable tissue containing the selectable DNA sequences; and after at least one shoot has formed, the shoot is typically transferred to a second medium capable of producing roots from the shoot.

2.2 Exogenous Genes

An aspect of the invention relates generally to transgenic plants which express one or more exogenous genes transformed via *A. tumefaciens*. As used herein, the term "transgenic plants" is intended to refer to plants that have incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. It is contemplated that in some instances the genome of transgenic plants of the present invention will have been augmented through the stable introduction of the transgene. However, in other instances, the introduced gene will replace an endogenous sequence.

Exemplary genes which may be introduced include, for example, DNA sequences or genes from another species, or even genes or sequences which originate with or are present in the same species, but are incorporated into recipient cells by genetic engineering methods rather than classical reproduction or breeding techniques. However, the term exogenous, is also intended to refer to genes which are not normally present in the cell being transformed, or perhaps simply not present in the form, structure, etc., as found in the transforming DNA segment or gene, or genes which are normally present yet which one desires, e.g., to have overexpressed. Thus, the term "exogenous" gene or DNA is intended to refer to any gene or DNA segment that is introduced into a recipient cell, regardless of whether a similar gene may already be present in such a cell.

An initial step in the production of fertile transgenic plants is the obtaining of a DNA composition, e.g., vectors, plasmids, linear DNA fragments, and the like, a component of which is to be delivered to recipient monocotyledonous cells. DNA segments for use in transforming such cells will, of course, generally comprise the gene or genes which one desires to introduce into the cells. These genes can further include structures such as promoters, enhancers, polylinkers, or even regulatory genes as desired.

Vectors, plasmids, cosmids, YACs (yeast artificial chromosomes) and DNA segments for use in transforming such cells will, of course, generally comprise the either cDNA, gene or gene sequences which one desires to transform into the monocotyledonous plants. These DNA constructs can further include structures such as promoters, enhancers, polylinkers, or even regulatory genes as desired. The DNA segment or gene may encode either a native or modified protein or polypeptide, which will be expressed in the resultant recombinant cells, and/or which will impart an improved phenotype to the regenerated plant.

In order to improve the ability to identify transformants, one may desire to employ a selectable or screenable marker gene as, or in addition to, the expressible gene of interest. Marker genes code for phenotypes that allow cells which express the marker gene to be distinguished from cells that do not have the marker. Such genes may encode either a selectable or screenable marker, depending on whether the marker confers a trait which one can select for by chemical means, i.e., through the use of a selective agent (e.g., a herbicide, antibiotic, or the like). Many examples of suitable marker genes are known in the art and may be employed in the practice of the invention.

Selectable markers for use in connection with the present invention include but are not limited to an nptII gene; a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; or a methotrexate resistant DHFR gene.

Exemplary screenable markers include a β-glucuronidase or uidA gene (GUS) which encodes an enzyme for which various chromogenic substrates are known; a β-lactamase gene, a luciferase gene, a xylEe gene, an α-amylase gene; a tyrosinase gene, an α-galactosidase, or any such suitable screenable marker which is known to those of skill in the art.

In light of this disclosure, numerous other possible selectable and/or screenable marker genes will be apparent to those of skill in the art. Therefore, the foregoing discussion is intended to be exemplary rather than exhaustive. Although the present disclosure is exemplified in detail through the use of the nptII and GUS genes, the applicable techniques for making and using any other screenable or selectable marker gene will be within the skill in the art in light of the present disclosure.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance, increased yields, insect and disease resistance, physical appearance, food content and makeup, etc. For example, one may desire to incorporate one or more genes encoding insecticidal genes which can be introduced includes the *Bacillus thuringiensis* crystal toxin gene, which provides resistance to Lepidopteran and Coleopteran insects. Such genes are well-known to those of skill in the art and are contemplated to be useful in the practice of the transformation methods disclosed herein for monocotyledonous plants such as wheat.

2.3 Transgenic Plants

An important aspect of the present invention are compositions comprising fertile cultivated, transgenic wheat plants. In these plants, the genome has been augmented through the genomic introduction of a preselected genetic component, to give rise to a transgenic plant. The transgene generally comprises a genetic component which includes one or more exogenous genes positioned under the control of one or more preselected genetic control elements or promoters. Such a plant is preparable by the process described herein which includes preparing a DNA composition in vitro which includes the genetic component one desires to introduce into the wheat genome, then introducing the DNA into recipient wheat cells by *Agrobacterium* transformation. The genetic component typically comprises one or more of the selectable or screenable genes described above. Following transformation, wheat plants are regenerated from the cells which received the exogenous gene(s) and resulting fertile, transgenic plants may be obtained which have genomes augmented through the stable introduction of the genetic component.

In the process, the cells which are transformed may dedifferentiate, or continue to be dedifferentiated and grow in a dedifferentiated state for a period of time before undergoing differentiation and maturation into a plantlet. In preferred embodiments, the recipient cells comprise immature embryos, callus tissues, or, alternatively, suspension cells. The embryos may be freshly isolated from an immature caryopsis or, alternatively, isolated from an immature caryopsis and then treated prior to inoculation. The immature embryo may be isolated from said immature caryopsis on the same day of inoculation, or alternatively, may be one or two, or five or 10 or even more days prior to inoculation. The embryo may be an embryo that is 1 or 2 or even more days after anthesis, or alternatively, the caryopsis may be 1 or 2 or even more days post-anthesis.

When callus tissue is used as the recipient cells, the callus may be isolated from either an immature embryo or from non-embryonic cells. In certain aspects, it may be desirable to injure the embryo prior to transformation which may promote transformation efficiency.

Also disclosed is a fertile, transgenic wheat plant, whose genetic complement has been altered through the addition of a DNA composition comprising a preselected functional genetic element that includes a transgene selected from the group consisting of an nptII gene, a bla gene, a nptI, dhfr, aphIV, aacC3, aacC4 gene, and a GUS gene. Particularly preferred are genes encoding glyphosate resistance, or an acceptable marker gene such as an nptII gene.

Recipient cells may be co-transformed with more than one exogenous gene, and under such circumstances, the exogenous genes may positioned on a single DNA segment, or alternatively, on one or more plasmids each under a different control element. Particularly preferred plasmids are recombinant plasmids such as pMON18365, pMON32614, pMON30053, pMON25457, pMON30052 and pMON19450. The genes may be positioned under the control of a promoter such as a CaMV 35S, ubiquitin, rice actin or an enhanced CaMV 35S promoter. Where desirable, the DNA segments to be transformed may include additional 5' and/or 3' regions operatively linked to the genes.

2.4 Transgenic Progeny, Seeds and Derived Cell Lines

Other important aspects of the invention include the progeny of the transgenic plants prepared by the disclosed methods, as well as the cells derived from such progeny, and the seeds obtained from such progeny.

3. BRIEF DESCRIPTION OF THE DRAWINGS

The drawings form part of the present specification and are included to further demonstrate certain aspects of the present invention. The invention may be better understood by reference to these drawings in combination with the detailed description of specific embodiments presented herein.

FIG. 1 shows the structure of pMON18365 which is an example of the plasmid harbored in *Agrobacterium* that was used in this invention. In the T-DNA region, both GUS and nptII genes are driven by an enhanced 35S promoter and an intron maize HSP70 intron. The GUS gene also contains two introns.

FIG. 11 shows the general protocol for transformation of immature embryos using the methods disclosed herein. d represents day, w represents week.

FIG. 12 shows the general protocol for transformation of suspension cells using the methods disclosed herein.

Figure 1:
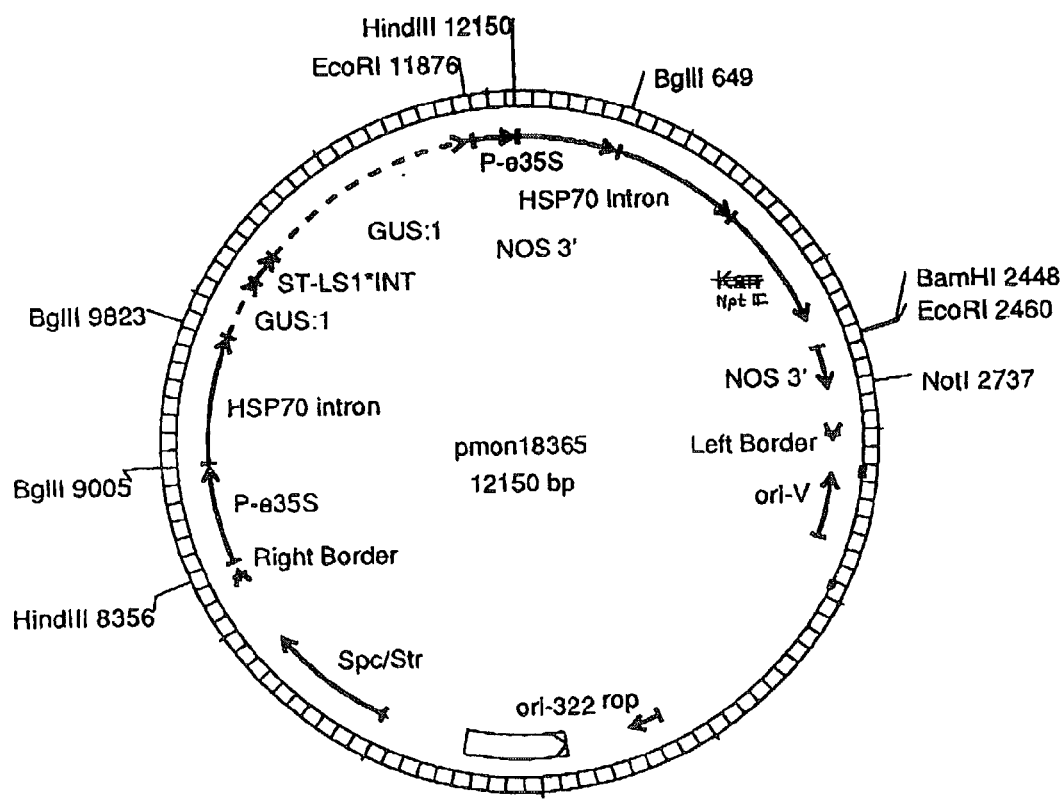

4. DESCRIPTION OF ILLUSTRATIVE EMBODIMENTS 4.1 Some Advantages of the Invention

Those having skill in the art will appreciate the many advantages of the methods and compositions provided by the present invention. A few such advantages may be summarized as follows:

4.1.1 Achievement of Efficient Transformation Using Regular Binary Vector

A regular binary vector pMON18365 was used with all the experiments in this invention. Efficient transformation was achieved in most of the experiments. The fact suggested that super binary vector may not be necessary, whereas it has been shown to be essential for achieving high transformation of maize (Ishida et al., 1996).

4.1.2 Transformation Using Different Types of Explants

Different types of explants, immature embryos, embryogenic callus and suspension cells, were used as explants for *Agrobacterium* infection in this invention. Stable transformants (colonies from the suspension cells and plants from the embryos and embryogenic callus) were generated from all of them, which made this invention superior to other published transformation systems via *Agrobacterium*, such as the system on maize (Ishida et al., 1996) in which only freshly isolated immature embryos could be used to produce transgenic plants.

4.1.3 Efficient and Rapid Production of Stable Transformants

A high efficient GUS gene expression was observed among the explants shortly after the *Agrobacterium* infection as illustrated in Tables 4 and 7. In the case the suspension cells were inoculated, approximately 200 stable transformants (colonies) could be recovered from 1 ml of the cells after 40–60 d selection on a medium containing a selective agent, such as G418. Transformed plantlets could be developed from infected immature embryos and callus pieces on a G418-containing medium a few weeks after inoculation. It took only approximately 3 months from the *Agrobacterium* infection to plants in soil. Among the experiments which generated transgenic plants, the stable transformation efficiency ranged from 0.3 to 4.3% (number of transgenic events/number of explants inoculated) (Table 5), which was comparable or higher than published ones using other transformation systems (Vasil et al., 1992, 1993; Weeks et al., 1993; Nehra et al., 1994; Becker et al., 1994; Zhou et al., 1995). The transgenic plants had normal morphology and completely fertile.

4.1.4 Mendelian Segregation of the Transgene in the Progeny

The transgene expression has been studied in the progeny ($R_1$ generation) of 4 primary transformed plants from 2 events. The GUS activity was observed in approximately ¾ of the individual (seeds and plants) of $R_1$ generation (Table 6) which indicated that the gene was transmitted to the progeny in a Mendelian fashion. No abnormalities were observed among the plants.

4.1.5 Production of Regenerable Transgenic Plants

A total of 9 events have been identified from 5 studies (7 different treatments) (TABLE 3). Southern analysis has been performed on 5 plants from 3 of the events from ExpAG2 and AG13. The results indicated that all 5 plants had the transgenes integrated into the genome. Plants from 6 other events (from ExpAG22, AG25 and AG30) were identified by the GUS histochemical assay and they are either in soil or in Sundae cups. All of them had very high to moderate GUS activity. The transformation efficiencies from 2 studies were 2.7 and 2.1%, respectively.

All events were generated from inoculated embryogenic callus tissue or pre-cultured immature embryos(IEs) (TABLE 4). The inoculation methods and conditions also varied among the studies. The results have indicated that Agrobacterium-mediated wheat transformation is repeatable and embryogenic callus tissue and pre-cultured IEs are suitable explants for Agrobacterium infection.

4.1.6 The 3:1 Segregation of GUS Activity in the $R_1$ Progeny $R_1$ plants from 3 transgenic plants from ExpAG13 (TABLE 3) have been produced by germinating the $R_1$ immature embryos in vitro. Plants were moved to soil, and GUS activity was in the $R_1$ progeny, the immature seeds with the embryos removed were cut to two halves longitudinally and used for the GUS histochemical assay. Scutellum tissue was also taken for the GUS assay from some of the germinating embryos. The maternal tissue, pericarp, of each seed was GUS-positive as expected. However, the aleurone layer of the seeds and scutellum tissue of the embryos segregated to GUS-positive or GUS-negative. The ratio of GUS-positive to GUS-negative plants was not significantly different from 3:1 by $\chi 2$ test (TABLE 2), indicating that the transgene was most probably inserted into a single locus.

TABLE 3

Transgenic Events Generated by Agrobacterium-Mediated Transformation

| Exp-Trt | Explant | #Pieces | Inoculation (%)[2] | # Event (plant)[1] | TE |
|---|---|---|---|---|---|
| AG2-05 | 3-w callus | 73 (large) | 3 h, vacuum infiltration | 2(2) | 2.7 |
| AG13-03 | 2-w callus | 47 (large) | vacuum inoculation | 1(3) | 2.1 |
| AG22-05 | 10-d callus | 239 (small) | 3 h, soaking | 1 | NA |
| AG22-06 | 25-d callus | 308 (small) | 3 h, soaking | 1 | NA |
| AG25-24 | 6-d IEs | 40 | 3 h, soaking | 1 | NA |
| AG30-02 | 3-d IEs | 98 | 3 h, soaking | 1 | NA |
| AG30-05 | 3-d IEs | 104 | 3 h, soaking | 2 | NA |

TABLE 4

GUS Activity in Aleurone Layer or Scutellum in Progeny Seeds of $R_0$ Plants

| $R_0$ Plant | # $R_1$ Seeds Assayed | # GUS-positive Seeds | # GUS-negative Seeds | chi square value[1] |
|---|---|---|---|---|
| AG13-03-02-01 | 31 | 22 | 9 | 0.27 |
| AG13-03-02-02 | 28 | 22 | 6 | 0.19 |
| AG13-03-02-03 | 124 | 96 | 28 | 0.387 |

[1]This value was calculated based on the hypothesis of 3:1 segregation. The critical value at $\alpha = 0.05$ and df = 1 was 3.84, larger than anyone of the chi square values in the table. Therefore, all the segregation ratios were not significantly different from hypothesized 3:1.

4.1.7 Methods Comprising EPA- and FDA-Approved Selectable Markers

While many of the disclosed methods for related grains have relied on hygromycin phosphotransferase (HPT) as the selectable marker, the present invention overcomes this limitation by using nptII as the selectable marker.

The nptII gene (which encodes neomycin phosphotransferase) is the most widely-accepted selectable marker in the art, and it has been approved by the Environmental Protection Agency as a pesticidal inert. Likewise, its approval by the Food and Drug Administration as an indirect food additive makes such a marker superior to the use of markers such as hygromycin, which have not been similarly approved by these agencies.

4.2 Differences from Systems Developed for Rice and Maize

The present invention differs considerably from methods described recently in other cereal grains. Unlike previous methods used for the transformation of rice, the present methods do not require high osmotic treatment for inoculation. Likewise, the present invention differs from the methods described for transformation of maize in that it is not limited to using only freshly-isolated immature embryos as explants. The present invention also works well for pre-cultured immature embryos or callus tissue, and is not limited to freshly-isolated embryonic tissue.

Another important distinction from previous work is that the methods of the present invention are applicable using standard binary plasmids which are well-known in the art, and do not rely on the construction and use of "super" binary plasmids as disclosed in earlier reports. The binary plasmid is the most common type used for most dicotyledonous plant transformation methods, and are readily available to those of skill in the art for use in the methods disclosed herein.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5. EXAMPLES

5.1 Example 1

Transformation Using Immature Embryos

5.1.1 Explant Preparation

A spring wheat *Triticum aestivum* cv. Bobwhite was used throughout this study. Stock plants were grown in an environmentally controlled growth chamber with 16-h photoperiod at 800 μmol $m^{-2}s^{-1}$ provided by high-intensity discharge (HID) Sylvania lights (GTE Products Corp., Manchester, N.H.). The day/night temperatures were 18/16° C. Immature caryopses were collected from the plants 14-d after anthesis. Immature embryos (IEs) were dissected aseptically and cultured on one of the following pre-culture media before inoculation: 1) semisolid callus induction medium CM4 or CM4C (TABLE 5) for 1–6 d; 2) liquid CM4C supplemented with 0.25 M raffinose and mannitol, respectively, for 1 d; 3) liquid CM4 medium with ¹/₁₀ strength of the MS salts and supplemented with 10 g/l glucose, 3.9 g/l MES for 1 to 3 h. All the cultures were conducted at the temperature of 23–25° C.

5.1.3 Inoculation and Co-Cultivation

The IEs temporarily maintained in the liquid pre-culture medium 3 were transferred into *Agrobacterium* cell suspension in petri dishes (25×100 mm). The ratio between *Agrobacterium* and IEs is about 30 ml: 200 IEs. A surfactant, Silwet® (Monsanto, St. Louis, Mo.), was added to the inoculation medium with a concentration of 0.01–0.075%. The inoculation was performed at 23–25° C. for 3 h in dark. After inoculation, the *Agrobacterium* was removed by vacuum or using a transfer pipette, and the IEs were placed on the co-culture medium, CM4 or CM4C with ¹/₁₀ strength of the MS salts and 1.5 mg/l extra 2,4-D and supplemented with 10 g/l glucose and 200 μM acetosyringone. The embryos were placed with scutellum-side up and were co-cultured with *Agrobacterium* for 2–3 d at 25° C. in the dark. The Pre-cultured immature embryos (cultured on medium 1 to 6 d) were inoculated with *Agrobacterium* with one of the following methods: 1) Immersing in the *Agrobacterium* cell suspension for 1–3 h. 2) The IEs were immersed in the *Agrobacterium* cell suspension in Petri dishes or cell culture clusters, which were then placed in a dessicator and vacuumed for 3 h using an in-house vacuum system. Silwet® at 0.01% was added to the inoculation

TABLE 5

Supplemental Components Basic Media[1]

| Components | CM4 | CM4C | MMS.2C | MMS0C | MS1WSM[4] | MS2WCM[4] |
|---|---|---|---|---|---|---|
| 2,4-D (mg/l) | 0.5 | 0.5 | 0.2 | — | 1.0 | 2.0 |
| Pichloram (mg/l)[2] | 2.2 | 2.2 | — | — | — | — |
| Maltose (g/l) | 40 | 40 | 40 | 40 | — | — |
| Sucrose (g/l) | — | — | — | — | 20 | 20 |
| Glutamine (g/l) | 0.5 | 0.5 | — | — | — | — |
| Magnesium Chloride (g/l) | 0.75 | 0.75 | — | — | 0.75 | 0.75 |
| Casein Hydrolysate (g/l) | 0.1 | 0.1 | — | — | — | — |
| MES (g/l) | — | 1.95 | 1.95 | 1.95 | — | — |
| Ascorbic Acid (mg/l)[2] | — | 100 | 100 | 100 | — | — |
| I-Asparagine (g/l) | — | — | — | — | 0.15 | 0.15 |
| Thiamine HCl (mg/l) | — | — | — | — | 0.5 | 0.5 |
| Gelling agent (g/l)[3] | 2(P) | 2(P) | 2(G) | 2(G) | — | 2(P) |

[1]All media contain basal salts (MS basal salts) and vitamins (MS vitamins) from Murashige and Skoog (1962) medium unless mentioned specifically. The pH in each medium was adjusted to 5.8
[2]Filter-sterilized and were added to the medium after autoclaving.
[3]Phytagel ™ (P) or Gelrite ® (G).
[4]No MS vitamins were present in the medium.

5.1.2 *Agrobacterium* Culture

Disarmed *Agrobacterium tumefaciens* strain C58 (ABI) harboring binary vector pMON18365 (FIG. 1) were used for all the studies. pMON18365 contains the GUS (uidA) gene with an intron and nptII gene as a selectable marker inside the T-DNA (transfer DNA) region. Both genes were under control of an enhanced CaMV 35S promoter. Cultures of *Agrobacterium* were initiated from glycerol stocks and grown overnight at 25–26° C. on a rotary shaker (150 rpm) in liquid LB medium (Miller, 1972) containing 50 mg/l each of kanamycin, streptomycin and spectinomycin, 25 mg/l chloramphenicol and 200 μM acetosyringone, to mid log phase ($OD_{660}$=1–1.5). *Agrobacterium* cells were collected by centrifugation and resuspended in an inoculation medium, CM4 or CM4C (TABLE 9) with ¹/₁₀ strength of the MS salts and supplemented with 10 g/l glucose and 200 μM acetosyringone. The *Agrobacterium* cell density was adjusted to $OD_{660}$ 2 for inoculation.

medium in some of the studies. After inoculation, the immature embryos were blotted on sterile filter papers and then transferred to one of the following media for co-cultivation: 1) semisolid CM4 or CM4C medium (TABLE 5) supplemented with 10 g/l glucose and 200 μM of acetosyringone; 2) liquid or semisolid CM4C medium with ¹/₁₀ strength of the MS salts and supplemented with 10 g/l glucose and 200 μM of acetosyringone. A filter paper (Whatman No. 1) was layered on the medium in some of the studies; 3) liquid CM4 or CM4C with ¹/₁₀ strength of the MS salts and 3.9 g/l MES and supplemented with 10 g/l glucose and 200 μM of acetosyringone. The immature embryos were placed on the medium or on the filter paper with scutellum-side up. To culture the embryos in a liquid medium, each culture plate was prepared by adding 8 ml of the liquid medium to a Petri dish (15 mm×100 mm) containing 6 pieces of Whatman No1 filter paper (8.5 cm). The explants were co-cultured with *Agrobacterium* at 24° C. in the dark for 2 to 3 d. After co-culture, the immature embryos were rinsed with liquid CM4 or CM4C medium supplemented with 500 mg/l carbenicillin (delay medium). The infected immature embryos were cultured on the solid delay medium for 2–5 d. The general protocol for these transformation methods is given in FIG. 6.

5.1.4 Efficiency of T-DNA Delivery

The efficiency of T-DNA delivery was measured by transient GUS expression assay after 2–3 d delay of selection. High levels of transient GUS expression were observed for most of studies, indicating that the T-DNA delivery was very efficient. The effect of Silwet® on the T-DNA delivery when included in the inoculation medium was extensively investigated on various explants. As shown in TABLE 6, Silwet® at 0.05–0.1% significantly enhanced the transient GUS expression on the freshly isolated IEs. Similar results were also observed using pre-cultured IEs and embryogenic callus as explant for inoculation. For the immature embryos pre-cultured for 1 or 2 d, the GUS spots were located mostly along the edge of the scutellum from which less embryogenic callus developed from. Tie GUS spots, however, were found in the callusing areas on the embryos pre-cultured 3 d or longer.

TABLE 6

Effect of Surfactant on GUS Expression When Present in Inoculation Medium[1]

| Silwet (%) | GUS-positive spots/explant | No. of explants w/GUS-positive spots/total explant (%) |
|---|---|---|
| 0.00 | 7.8 | 11/34 (32) |
| 0.01 | 17.6 | 15/19 (79) |
| 0.05 | 149 | 13/13 (100) |
| 0.1 | 111 | 8/8 (100) |
| 0.5 | 1 | 1/1 (100) |

[1]The explants were IEs isolated a few of hours before inoculation.

5.1.5 Selection and Plant Regeneration

After 2 to 5 d on the delay medium, the *Agrobacterium*-infected immature embryos were transferred to the callus induction medium, CM4 or CM4C (TABLE 5) medium with 25 mg/l G418 and 250 mg/l carbenicillin. The immature embryos were cultured for 2 to 3 weeks for callus induction before being transferred to the first regeneration medium, MMS.2C (TABLE 5) with 25 mg/l G418 and 250 mg/l carbenicillin. At transfer to the regeneration medium, each piece of callus was divided into several small pieces (~2 mm). Two weeks after the cultures on the first regeneration medium, young shoots and live callus tissue were transferred to the second regeneration medium, MMS0C (TABLE 5) with the same concentrations of G418 and carbenicillin. Plantlets, which were confirmed later true transformants, grew vigorously and formed strong root systems in this medium. However, there were some plantlets showing some resistance to G418 at this stage. They could grow well and form one or a few of roots, although they did not grow as vigorously as the true transformants. When the plants were about 3 cm or longer, they were transferred to Sundae cups (Sweetheart Cup Company, Chicago, Ill.) containing the second regeneration medium as above for further growth and selection. Leaf samples were taken from some of the plantlets for the GUS histochemical assay at this stage. However, the plantlets, which appeared resistant and showed no GUS activity at this stage, were not eliminated. During growth in the cups, most of the non-transformants died or showed signs of susceptibility to G418. The plants highly resistant to G418 (growing vigorously with strong root system) were moved to soil before they reached the top of the cups. All the plants originated from the same embryo were considered as siblings from the same event.

5.1.6 Confirmation of the Transgenic Nature of the Plants

The plants were grown in a environmentally controlled growth chamber under the same growth conditions as described above. Since it took only approximately 3 months from inoculation to transferring most of the plants to soil, no visible abnormalities, which are usually associated with plants having prolonged in vitro culture period, were observed among the plants. The plants were completely fertile. Each plant was examined by one or more of the following methods:

(1) The GUS histochemical assay (Jefferson, 1987) using different parts of the plants.

(2) Biological assay (leaf bleach assay). Before heading, leaf samples (~5–7 mm long) were taken from the youngest fully expanded leaves and were placed in wells of 24-well cell culture clusters (Costar Corporation, Cambridge, Mass.). Each well was filled with 0.5 ml water solution composed of 300 mg/l paromomycin (Sigma) and 100 mg/l Benlate (a fungicide made by Du Pont) or 100 mg/l Benlate alone. Three leaf samples from the same leaf of each plants were placed in 2 wells containing paromomycin and Benlate and 1 well containing Benlate alone, respectively. Leaf samples from the non-transformed Bobwhite plants were used as negative controls. The samples were vacuum-infiltrated in a dessicator using an in-house vacuum system for 5 min and then the cluster were sealed very well with Parafilm® before being placed under light (140 $\mu$mol m$^{-2}$s$^{-1}$). The results were determined 60 h later. The leaf samples which were highly resistant to paromomycin remained green in most area except the two edges (<1 mm wide), which indicated that the plants had the functional nptII gene. The leaf samples from the plants without the gene or with the non-functional gene were bleached out completely by paromomycin as the negative controls, or had only small patches of green areas.

(3) Southern hybridization analysis (Southern, 1975). Genomic DNA were isolated from leaf tissue of the plants following the method of Shure et al. (1983). Fifteen $\mu$g of genomic DNA was digested with restriction endonuclease BamHI and fractionated on a 0.8% agarose gel. The DNA was transferred to Hybond N membranes (Amersham, Arlington Heights, Ill.) according to standard procedures (Sambrook et al., 1989). The probe for detecting the nptII gene was prepared by gel purifying a 977 bp NcoI fragment from plasmid pMON18365 (FIG. 1). The fragment was labeled with $^{32}$P dCTP using random primer labeling kit (Prime-It II® from Stratagene®, La Jolla, Calif.), to a specific activity of 2.6×10$^9$ cpm/$\mu$g. The membrane was hybridized for 14 h at 42° C. in a solution containing 50% formamide, 5×SSC, 5×Denhardt's, 0.5% SDS, 100 $\mu$g/ml tRNA. The condition of the final wash was 0.1% SSC and 0.1% SDS at 60° C. for 15 min.

5.1.7 Efficiency of Stable Transformation

The number of the transgenic events in each study was determined after the plants were assayed as described above. The transformation efficiency (number of events/number of immature embryos) varied from study to study and among different treatment conditions that generated transgenic plants (TABLE 7). However, they were comparable with or higher than any published wheat transformation efficiencies (Vasil et al., 1992, 1993; Weeks et al., 1993; Nehra et al., 1994; Becker et al., 1994;Zhou et al., 1995).

TABLE 7

Stable Transformation Efficiencies in the Production of Transgenic Wheat

| Experiment-Treatment | Explant | Number of IEs or callus pieces (A) | Number of transgenic events (B)[1] | Efficiency (B/A%) |
|---|---|---|---|---|
| AG2-05 | 21-d callus, intact | 73 | 2 | 2.7 |
| AG13 | 14-d callus, intact | 47 | 1 | 2.1 |
| AG22-05 | 10-d callus, ~2 mm | 239 | 1 | 0.4 |
| AG22-06 | 25-d callus, ~2 mm | 308 | 1 | 0.3 |
| AG22-11 | 10-d callus, ~2 mm | 232 | 1 | 0.4 |
| AG25-24 | 6-d IEs | 40 | 1 | 2.5 |
| AG27-15 | 1-d IEs | 23 | 1 | 4.3 |
| AG29-04 | 5-d IEs | 97 | 1 | 1.0 |
| AG30-02 | 3-d IEs | 98 | 1 | 1.0 |
| AG30-05 | 3-d IBs | 104 | 2 | 1.9 |
| AG30-08 | 3-d IEs | 36 | 1 | 2.8 |
| 9528 | 0-d IEs | 160 | 1 | 0.6 |
| 9531 | 17-d callus, intact | 50 | 1 | 2.0 |
| 9602 | 0-d IEs | 250 | 3 | 1.2 |
| 9604 | 0-d IEs | 700 | 1 | 0.14 |
| 9608 | 0-d IEs | 124 | 1 | 0.8 |
| 9609 | 0-d IEs | 140 | 2 | 1.4 |
| 9614 | 0-d IEs | 38 | 1 | 2.6 |
| 9620 | 15-d callus, intact | 110 | 3 | 2.7 |

[1]Each transgenic event had one or more plants.

5.1.8 Progeny Analysis of the Transgenic Plants

Immature caryopses were harvested from the primary transgenic plants ($R_0$ generation) with both nptII and GUS activities approximately 20 days after anthesis. The immature embryos were isolated and cultured on MMSOC medium (TABLE 5) for plant germination (approximately 1 week in Petri dishes and another week in Sundae cups with the same medium). Each of the immature caryopses with the embryos removed was cut to two halves longitudinally and moved to a well in 96-well cell culture clusters (Costar Corp., Cambridge, Mass.) for the GUS histochemical assay as described above. All the half caryopses were examined under microscope to determine the GUS activity in different areas. Part of the scutellum tissue was also taken from each germinating embryo for the GUS assay. After the plants ($R_1$ generation) were moved to soil approximately 2 weeks after germination, the GUS activities in the plants were determined by the GUS histochemical assay using leaf and flower tissues, respectively.

As expected, the maternal tissue, pericarp, of each immature caryopses showed GUS activity. However, in the aleurone layer most of the caryopses showed GUS activity, others not. The ratio of caryopses with GUS positive aleurone layer to ones with GUS negative aleurone layer was not significantly different from 3:1 by chi square test (TABLE 8). The data from the GUS assay on the caryopses matched well with the data on scutellum tissue and later with the GUS assay on leaf and flower tissue, although the GUS activity in aleurone layer and scutellum appeared much stronger than in leaf and flower tissues.

TABLE 8

Segregation of GUS Activity in $R_1$ Seeds and Plants

| $R_0$ plants | Number of R1 seeds (plants) assayed | Number of GUS-positive | Number of GUS-negative | chi square value |
|---|---|---|---|---|
| 16612 | 31 | 22 | 9 | 0.27 |
| 16613 | 28 | 22 | 6 | 0.19 |
| 16614 | 124 | 96 | 28 | 0.387 |
| 16953 | 128 | 103 | 25 | 2.04 |

[1]This value was calculated based on the hypothesis of 3:1 segregation. The critical value at $\alpha = 0.05$ and $df = 1$ was 3.84, larger than any one of the chi square values in the table. Therefore, all the segregation ratios were not significantly different from hypothesized 3:1.

5.2 Example 2

Transformation Using Embryogenic Callus

5.2.1 Explant Preparation

Immature embryos of wheat (*Triticum aestivum* L.) cv Bobwhite were isolated from the immature caryopsis 14 days after anthesis and cultured on callus induction medium CM4 or CM4C (TABLE 9) with scutellum-side up. After 10 days or longer, immature embryos developed into embryogenic callus. Each callus piece was approximately 5 mm or bigger. The callus pieces were inoculated with *Agrobacterium* without being broken down (intact), or only the most embryogenic callus sections were selected and broken down into small pieces (~2 mm) using fine-pointed forceps for inoculation.

5.2.2 Inoculation and Co-Cultivation

Callus pieces were inoculated with the *Agrobacterium* cell suspension prepared as described above, using one of the following methods:

1) Immersing the callus pieces in the *Agrobacterium* cell suspension for 3 h.

2) Immersing the callus pieces in the *Agrobacterium* cell suspension with vacuum infiltration for 3 h.

3) Intact callus pieces were placed on a piece of sterile filter paper saturated with the liquid inoculation medium. The callus pieces were inoculated as they were, or were pressed before inoculation using a sterile spatula until the callus pieces became "pancakes". Each piece of the filter paper holding the callus pieces was transferred to a 150-ml filter system (Corning, Inc., Corning, N.Y.) connected to an in-house vacuum system, or to a Buchner funnel connected to the vacuum system through a filter flask. With the vacuum system on, the *Agrobacterium* cell suspension was dropped onto the callus pieces (>1 ml over 6 callus pieces) slowly. After dropping the *Agrobacterium* suspension cells, vacuum was applied for another 10 min. The callus pieces inoculated with any one of the methods were transferred to Petri dishes (100×15 mm) each containing 6 pieces of Whatman filter paper (No. 1, 8.5 cm) saturated with 8 ml of the co-cultivation medium (CM4 or CM4C with 1/10 strength of the MS salts and supplemented with 10 g/l glucose and 200 μM acetosyringone). The plates were sealed well with Parafilm®. After co-culture with the *Agrobacterium* cells for 3 days, the callus pieces were washed with the liquid delay medium (CM4 or CM4C supplemented with 500 mg/l carbenicillin) and blotted on pieces of sterile filter paper to remove excess liquid. The callus pieces were cultured on the semisolid delay medium for 3 days before being transferred to the selective callus induction medium.

5.2.3 Efficiency of T-DNA Delivery

After co-culture with *Agrobacterium* or delay stage, samples of the callus pieces were randomly taken for the GUS histochemical assay (Jefferson, 1987). As shown in TABLE 11, most callus pieces assayed had GUS positive spots. In some studies (such as experiment AG13), every piece of callus assayed had GUS positive spots. The number of GUS positive spots in each piece of callus varied from a few of to approximately 100. In experiment AG13, another GUS histochemical assay was carried out two weeks after inoculation. All of the 16 pieces of callus assayed had some GUS positive spots and among them 7 pieces (44%) had growing GUS positive sectors, which suggested that transformed cells were proliferating.

TABLE 9

Efficiency of T-DNA Delivery as Indicated by GUS Histochemical Assay on Callus Pieces After Co-Culture

| Exp-Treatment | Explant | Number of IEs w/ GUS-positive spots (Total number of IEs assayed) | Number of spots on each GUS-positive IE |
|---|---|---|---|
| AG2-5 | 21-d callus, intact | 1/19 | 1–5 |
| AG13 | 14-d callus, intact | 25/25 | several - ~50 |
| AG22-5 | 10-d callus, ~2 mm | 6/15 | several |
| AG22-6 | 25-d callus, ~2 mm | 7/10 | a few - ~100 |
| AG22-11 | 10-d callus, ~2 mm | 12/20 | a few - dozen |

5.2.4 Selection and Plant Regeneration

The callus pieces, which were intact during inoculation, were cultured on the selective callus induction medium (CM4C supplemented with 25 mg/l G418 and 250 mg/l carbenicillin) as they were, or were broken down to several small pieces (~2 mm) at transfer to the medium. The inoculated small callus pieces were left intact and cultured on the medium. After 2 to 3 weeks, callus pieces were transferred to the regeneration medium. The regeneration procedure was the same as described in Example 1.

5.2.5 Transformation Efficiency

The regenerated plants showed no visible abnormalities and were completely fertile. All the plants were tested with the biological assay, GUS histochemical assay and/or Southern hybridization assay as described in Example 1. A total of 10 transgenic events have been generated from 7 experimental treatments using embryogenic callus at different ages (TABLE 9). The transformation efficiency (number of events/number of the callus pieces) ranged from 0.3 to 2.7%.

5.2.6 Progeny Analysis of the Transgenic Plants

The R1 plants were analyzed as described in Example 1.

5.3 Example 3

Transformation of Suspension Cells

5.3.1 Explant Preparation

Figure 7:
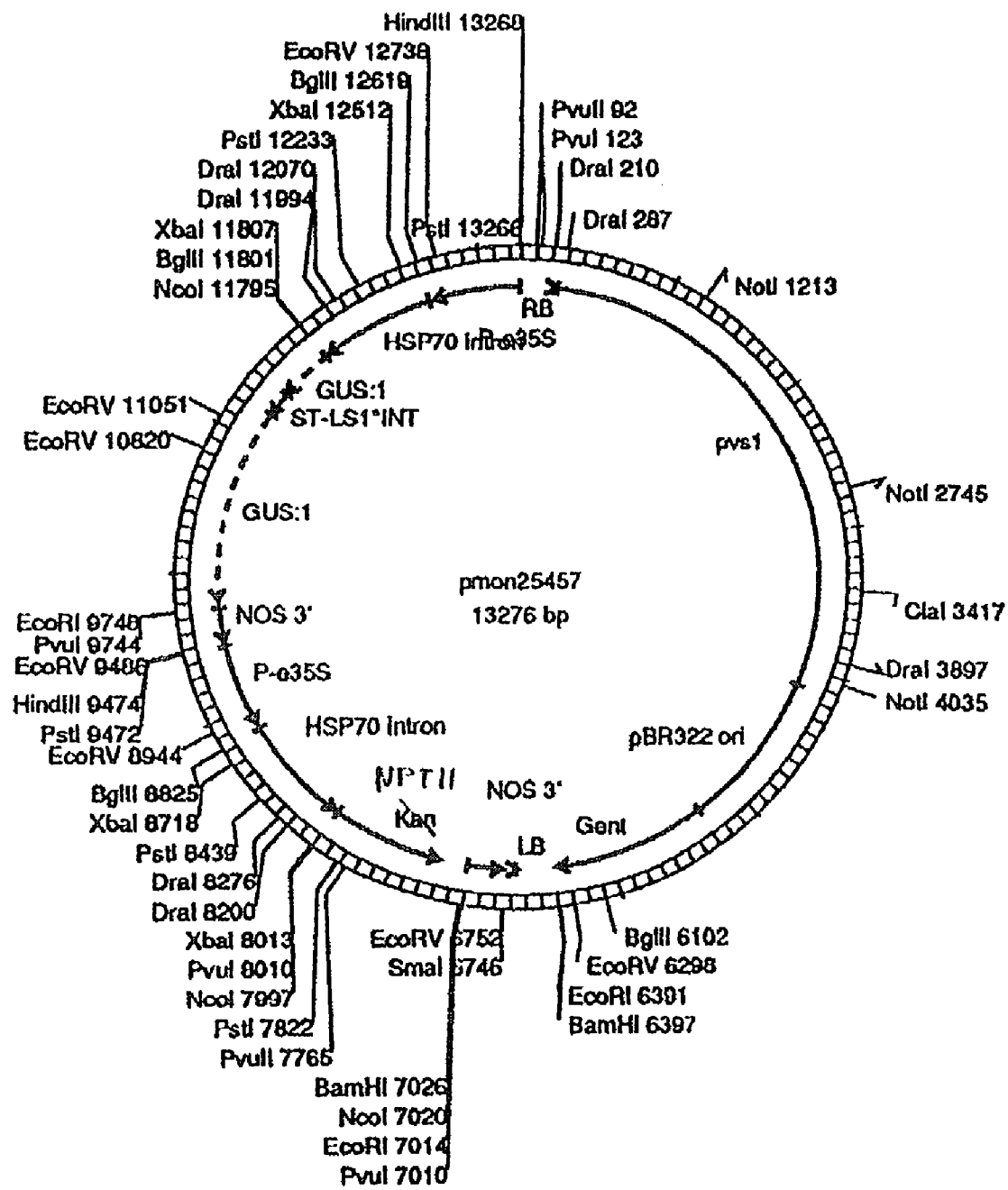
FIG. 7 shows the structure of pMON25457.

Wheat v. Mustang suspension cells were cultured in liquid MS1WSM (TABLE 9) at 28° C. in the dark on a rotary shaker (250 rpm). Cells harvested after 3 d subculture were used for inoculation with *Agrobacterium*. The general protocol for transformation of suspension cells is given in FIG. 7.

5.3.2 *Agrobacterium* Culture and T-DNA Delivery

The *Agrobacterium* culture method was essentially the same as described in Example 1. The *Agrobacterium* cell density was adjusted to $OD_{660}$ 0.5–1 in inoculation medium (CM4 medium with 1/10 strength of the MS salts and 3.9 g/l MES and supplemented with 10 g/l glucose and 200 μM acetosyringone. Liquid medium was removed from the wheat cell suspension culture by vacuum. Each ml of the wheat cells was mixed with 3 ml of the *Agrobacterium* cell suspension petri dishes (100×25 mm). The inoculation was performed at 23–25° C. for 30 min to 4 h. After inoculation, *Agrobacterium*-infected wheat cells were placed on a piece of sterile Whatman filter paper in petri dishes (100×15 mm). The filter paper was wetted with the liquid medium as described above. The co-culture plates were placed in the dark at 23–25° C. for 2 to 3 d.

5.3.3 Recovery of Transformed Colonies

After co-culture, the inoculated cells were transferred into liquid MS2WCM (TABLE 9) with 500 mg/l carbenicillin and cultured in flasks for 1 d with gentle agitation, and then plated on a piece of filter paper on the solid MS2WCM medium supplemented with either 25 mg/l G418 or 50 mg/l paromomycin and 250 mg/l carbenicillin for selection. Resistant colonies could be recovered after 40 to 60 d selection. The transformation was highly efficient based on the number of transformed colonies recovered. Routinely approximately 200 independently transformed colonies were recovered from 1 ml of inoculated cells.

5.3.4 Factors Influencing Transformation Efficiency

Three factors involved in inoculation and co-culture processes were found to significantly influence the transformation efficiency of suspension cells. The factors were inoculation and co-culture temperatures, inoculation and co-culture time period, and *Agrobacterium* cell density for inoculation. As shown in TABLE 10, the best inoculation and co-culture temperature is 23 to 25° C., and the transformation efficiency is significantly reduced at temperature 19° C. or 28° C. The best inoculation time period was 30 min (TABLE 11), and high transformation efficiency could be achieved with 2 or 3 d co-culture. The co-culture time period of 1 d or shorter significantly reduced the transformation efficiency. The best *Agrobacterium* cell density for inoculation was $OD_{660}$ 0.5 (TABLE 12). *Agrobacterium* density higher or lower than that reduced the transformation efficiency.

TABLE 10

Effect of Temperature During Inoculation and Co-Cultivation on Stable Transformation of Suspension Cells

| Temperatures (° C.) | Number of GUS-positive colonies/ml cell inoculated |
|---|---|
| 19 | 52.5 ± 19.36 |
| 23 | 290 ± 70.83 |
| 25 | 273 ± 65.43 |
| 28 | 132.5 ± 22.6 |

TABLE 11

Effect of Inoculation and Co-Culture Time on Suspension Cell Transformation

| Stage | Duration (h) | Number of GUS-positive colonies/ml cells inoculated |
|---|---|---|
| Inoculation | 0.5 | 351.25 ± 29.23 |
| | 1 | 178.5 ± 23.1 |
| | 2 | 186.75 ± 23.10 |
| | 3 | 202 ± 51.37 |

TABLE 11-continued

Effect of Inoculation and Co-Culture Time
on Suspension Cell Transformation

| Stage | Duration (h) | Number of GUS-positive colonies/ml cells inoculated |
|---|---|---|
| | 4 | 152.25 ± 29.68 |
| | 14 | 4 ± 0.82 |
| Co-culture | 24 | 53 ± 4.24 |
| | 48 | 232.5 ± 26.29 |
| | 72 | 258.5 ± 15.26 |

TABLE 12

Effect of Agrobacterium Cell Density on
Transformation of Suspension Cells

| Agrobacterium cell density ($OD_{660}$) | Number of GUS-positive colonies/ml of cells |
|---|---|
| 0.10 | 79 ± 4.97 |
| 0.25 | 174 ± 53.67 |
| 0.50 | 260.25 ± 45.33 |
| 1.00 | 172 ± 51.04 |
| 2.00 | 159 ± 70.06 |

5.3.5 Confirmation of Transformed Colonies

The transformation was confirmed by histochemical GUS assay as described. Samples from 51 G418 resistant colonies were assayed for GUS activity. Forty nine out of 51 colonies showed GUS positive. Among them, fifteen were sampled for Southern blot analysis. All the samples showed a strong hybridization signal to the nptII probe. These results may suggest that the co-expression frequency was close to 100%.

5.4 Example 4

Transformation of Suspension Cells 5.4.1 *Agrobacterium* Constructs

Figure 2:
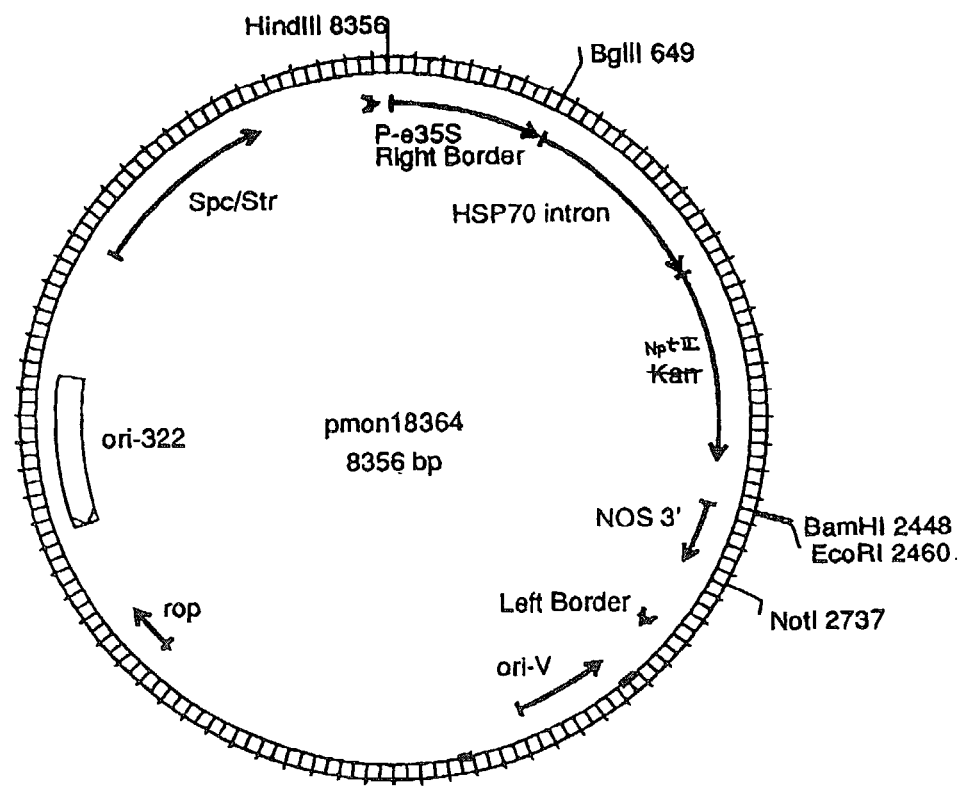
FIG. 2 shows the structure of pMON18364 which was used in the construction of pMON18365.
Figure 3:
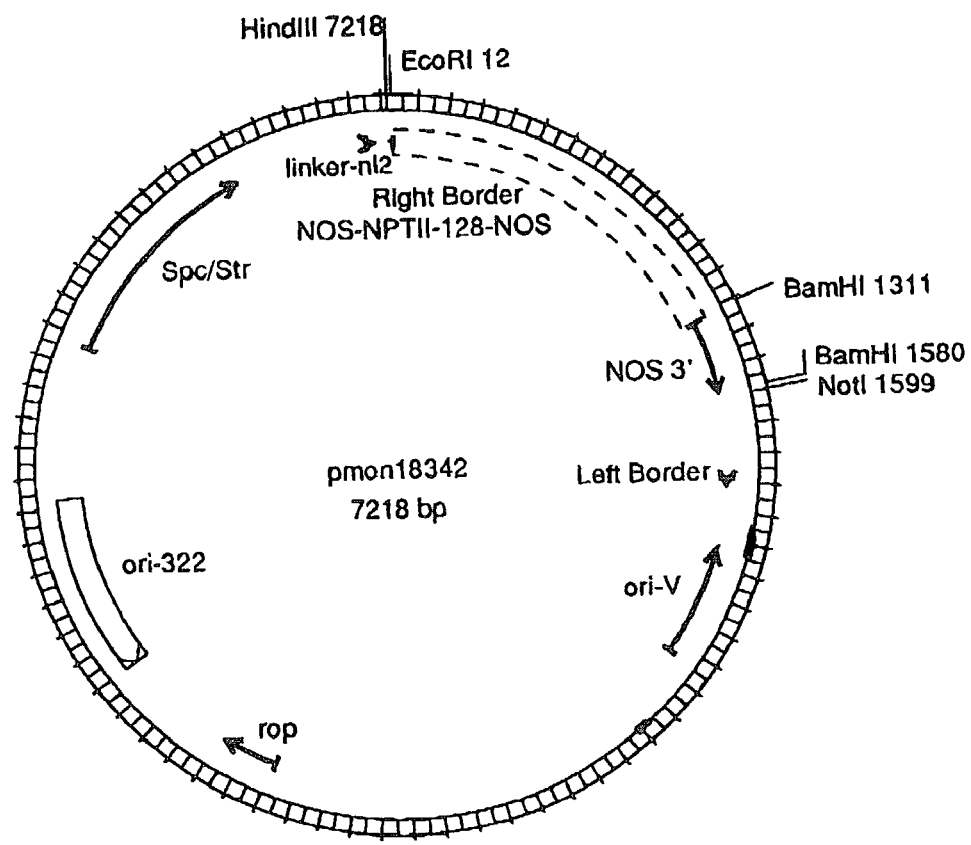
FIG. 3 shows the structure of pMON18342 which was used in the construction of pMON18365.
Figure 4:
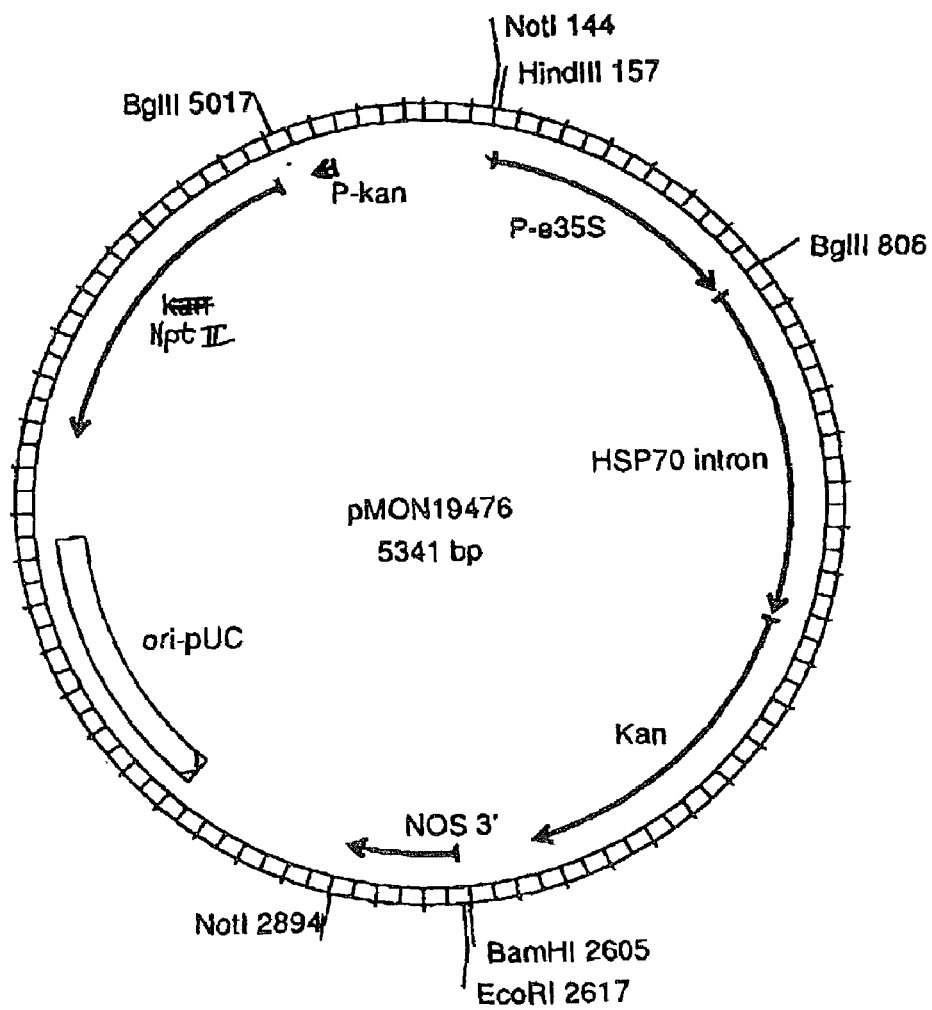
FIG. 4 shows the structure of pMON19476 which was used in the construction of pMON18365.
Figure 5:
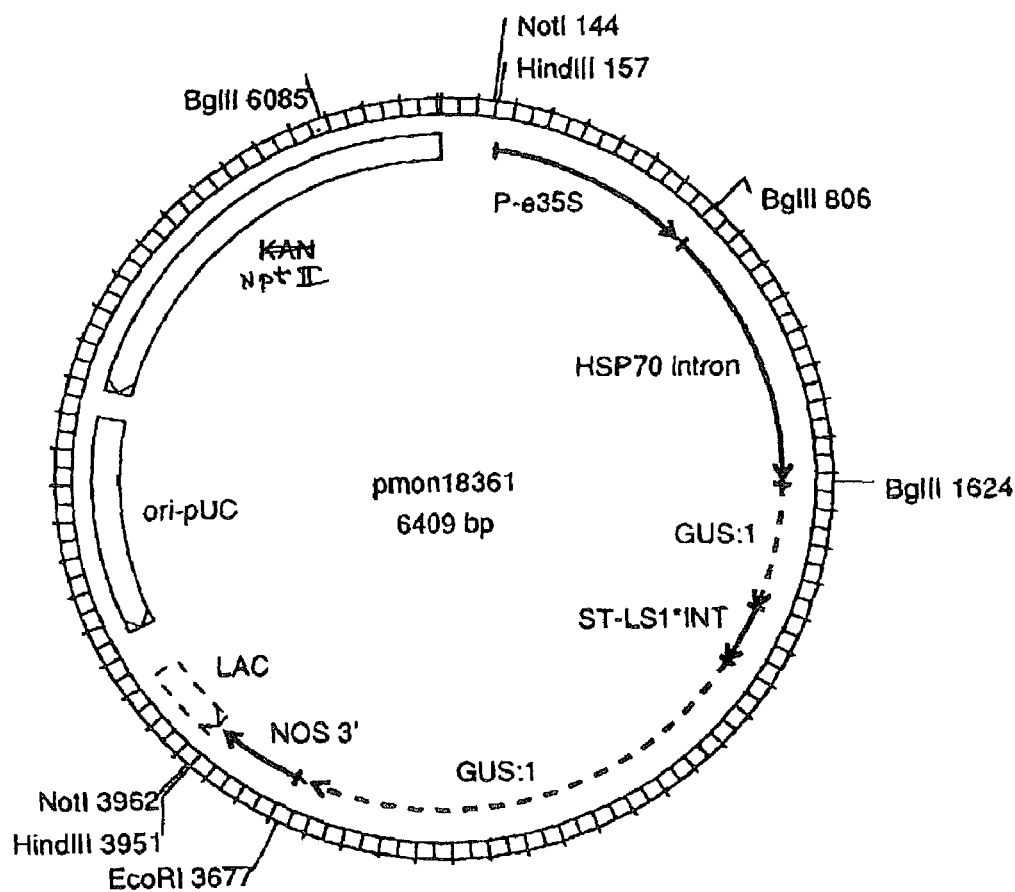
FIG. 5 shows the structure of pMON18361 which was used in the construction of pMON18365.

Plant transformation vectors similar to those derived from a Ti plasmid of *Agrobacterium tumefaciens*, such as those disclosed by Herrera-Estrella et al. (1983), Bevan et al. (1983), Klee et al. (1985) and EPO publication 120,516 (Schilperoort et al.) were constructed for use in wheat. The *Agrobacterium* binary vector for wheat, pMON18364 (FIG. 2), was constructed by the removal of the P-nos/nptII/nos 3' from pMON18342 (FIG. 3), by digesting pMON18342 with NotI and HindIII restriction enzymes to completion and isolation of the 5.7 kb fragment. This resulting 5.7 kb vector backbone fragment contains the ori-322 replication origin for replication in *E. coli* and the ori-V region for replication in *Agrobacterium*, bacterial resistance markers for spectinomycin and streptomycin selection. The P-e35S/hsp70 intron/kan/nos 3' chimeric fragment was isolated from pMON19476 (FIG. 4) by digesting to completion with NotI and HindIII restriction enzymes and gel isolation of the resulting 2.7 kilobase (kb) insert. pMON18364 the binary vector was constructed by ligation of the 2.7 kb NotI, HindIII P-e35S/hsp70 intron/kan/nos 3' fragment and the NotI, HindIII 5.7 kb vector backbone fragment using T4 DNA ligase. Ligation products were transformed into Novablue cells and selected for spectinomycin resistance. Transformed colonies from this unidirectional cloning were grown in liquid culture and DNA was analyzed for the presence of the P-e35S/kan/nos 3' chimeric gene by restriction digestion with HindIII, and EcoRV. For reporter gene constructs, the *Agrobacterium* binary vector containing the β-glucoronidase (GUS) gene was constructed by digesting pMON18361 (FIG. 5) with HindIII and isolation of the 3.8 kb fragment containing the P-e35S/hsp70 intron/GUS/nos 3' chimeric fragment and ligation of this fragment to HindIII digested pMON18364. Analysis of the resulting transformed colonies was performed with HindIII and orientation was verified with BglII, and XbaI digestions. The resulting construct is pMON18365 (FIG. 6): RB>P-e35S/hsp70 intron/GUS:ST-LS1 intron/nos 3'; P-e35S/HSP70 intron/nptII/nos>LB, where LB and RB are left and right *Agrobacterium* Ti plasmid transfer borders, respectively.

Other genes may be introduced in wheat; for example, wheat streak mosaic virus (WSMV) coat protein and Barley Yellow Dwarf Virus (BYVD) replicase conferring resistance to plant viruses. A suitable plant expression vector is pMON18365 or derivatives of similar binary vectors. A gene encoding the coat protein (CP) from WSMV may similarly be inserted into pMON18364 or pMON18365 using standard techniques. The recombinant vector containing the WSMV CP gene when transferred into wheat plants by the *Agrobacterium* mediated transformation method would be expected to confer resistance to the wheat plants from infection by WSMV. Similarly, a gene encoding the BYVD full-length replicase gene may be introduced into the same or similar *Agrobacterium* vector cassettes. The recombinant vector containing the BYDV full-length replicase gene when transferred into wheat plants by an *Agrobacterium* mediated transformation method would be expected to confer resistance to the wheat plants from infection by BYDV.

Figure 6:
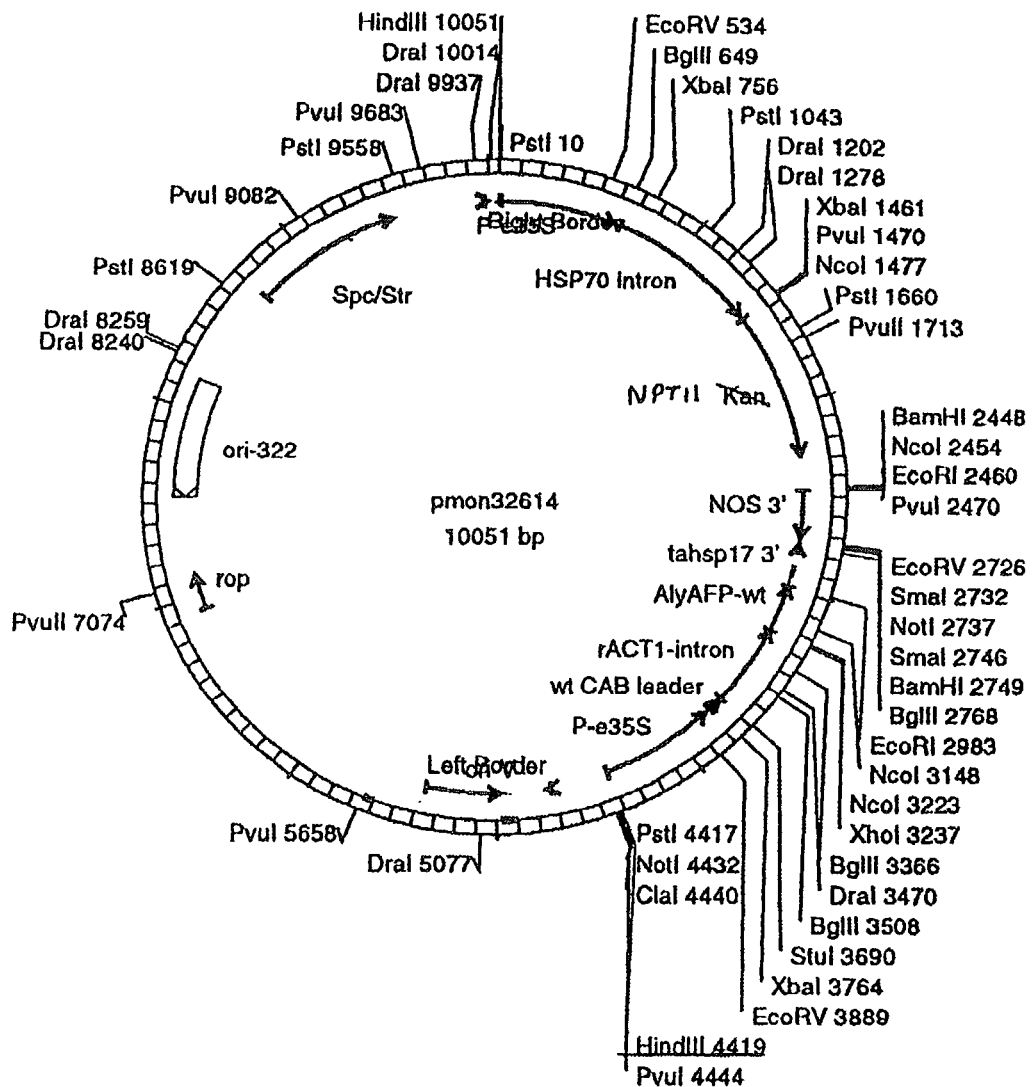
FIG. 6 shows the structure of pMON32614.

Genes encoding fungal resistance may also be introduced into *Agrobacterium* binary vectors such as pMON18364 and pMON32614 (FIG. 6). Antifungal protein genes such as those encoding Alfalfa or Alyssum antifungal proteins inserted into pMON18364 or pMON18365 as described above would allow engineering for fungal resistance into wheat by *Agrobacterium* mediated transformation for the production of transgenic plants. The resulting plants would be expected to exhibit resistance to Fusarium or other fungal or bacterial pathogens.

Genes that affect quality traits involved in carbohydrate quantity and composition in the kernel such as ADP glucose pyrophosphorylase (ADPGPP) expressed under the control of a kernel enhanced promoter or other tissue enhanced promoters could be inserted into a binary vector such as pMON18365 or derivatives. *Agrobacterium*-mediated transformation of wheat plants with this gene are expected to confer changes in the amount or quality of carbohydrates in the kernel or other tissues producing changes in the composition of matter.

Figure 8:
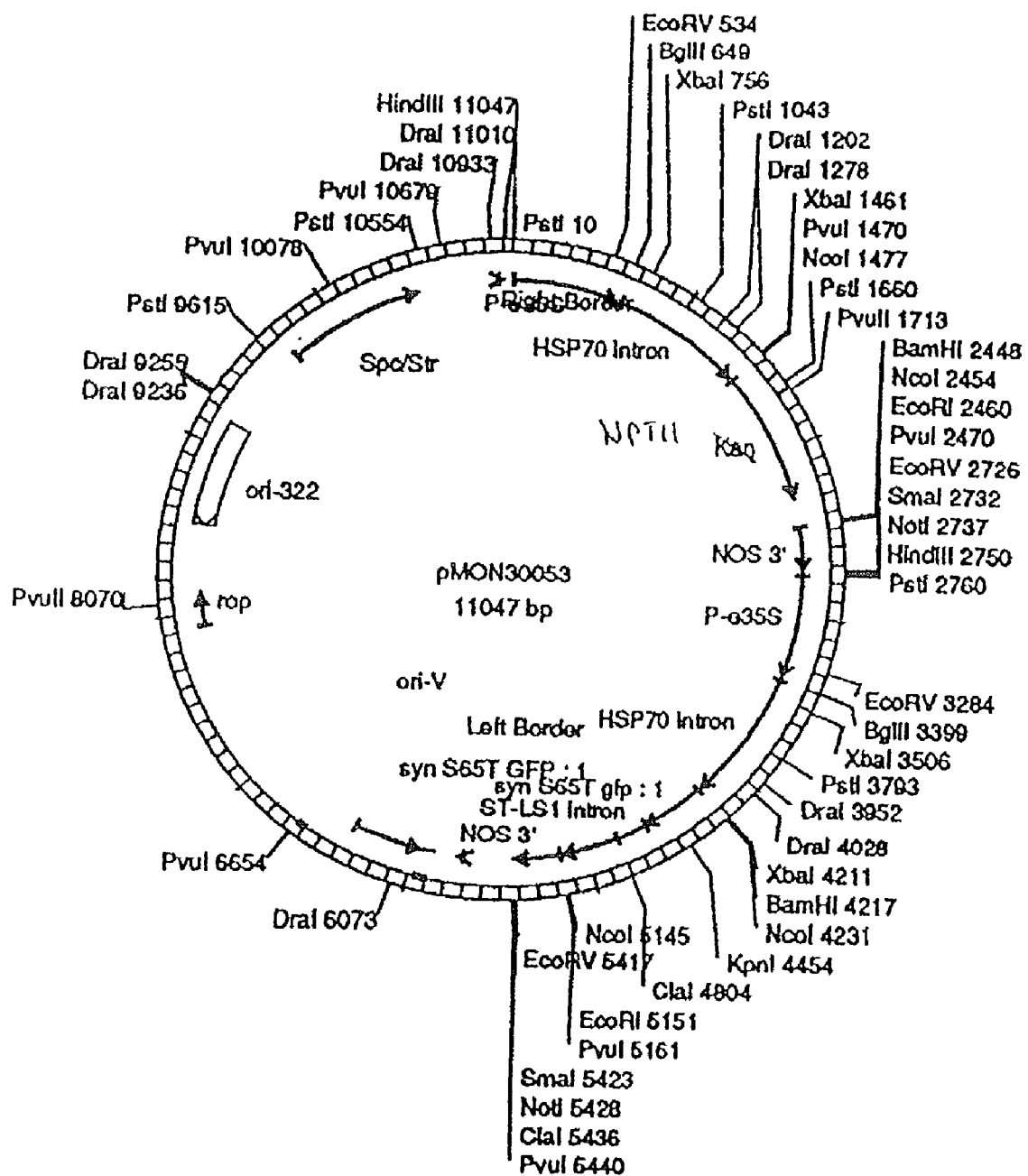
FIG. 8 shows the structure of pMON30053.
Figure 9:
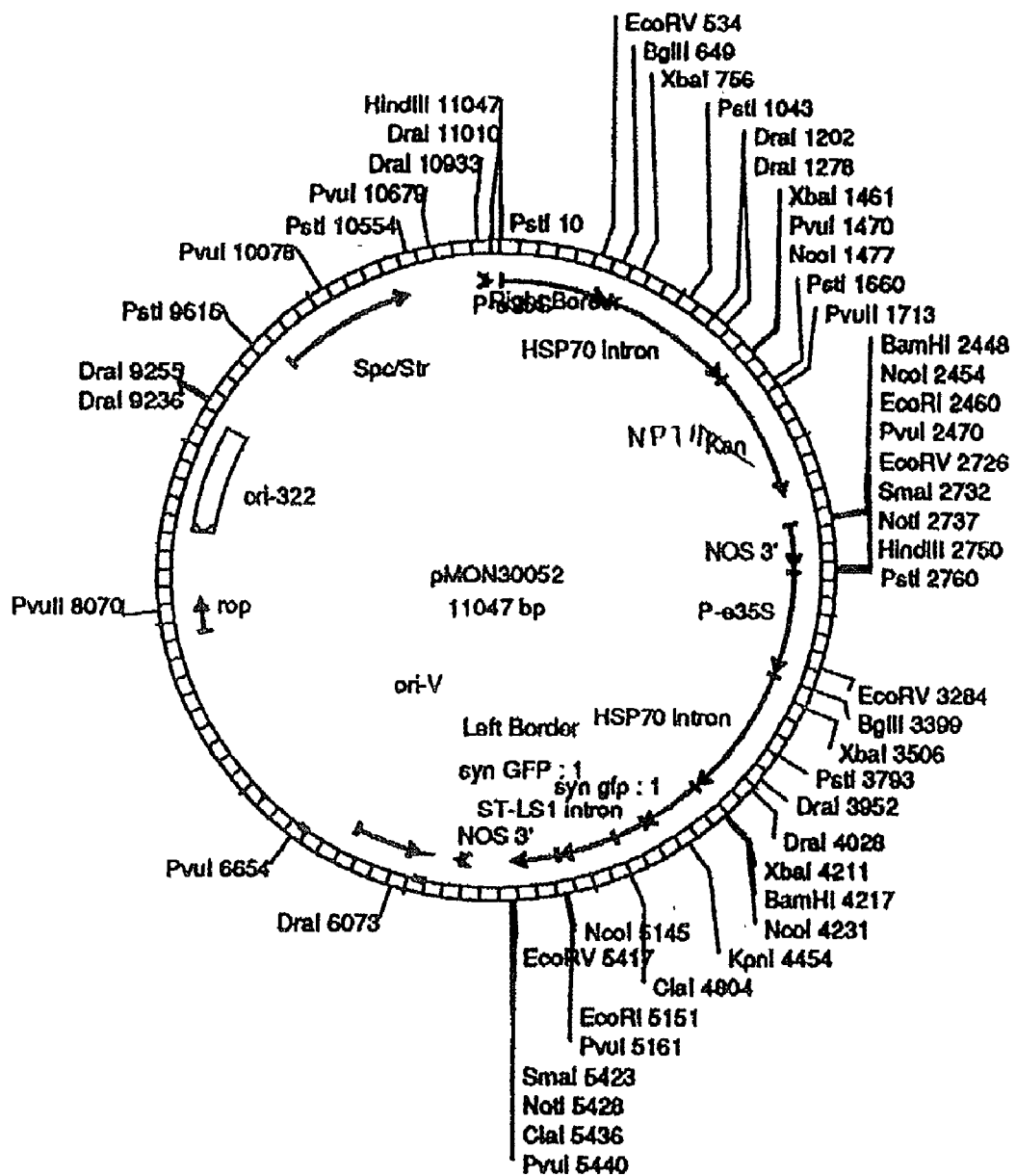
FIG. 9 shows the structure of pMON30052.
Figure 10:
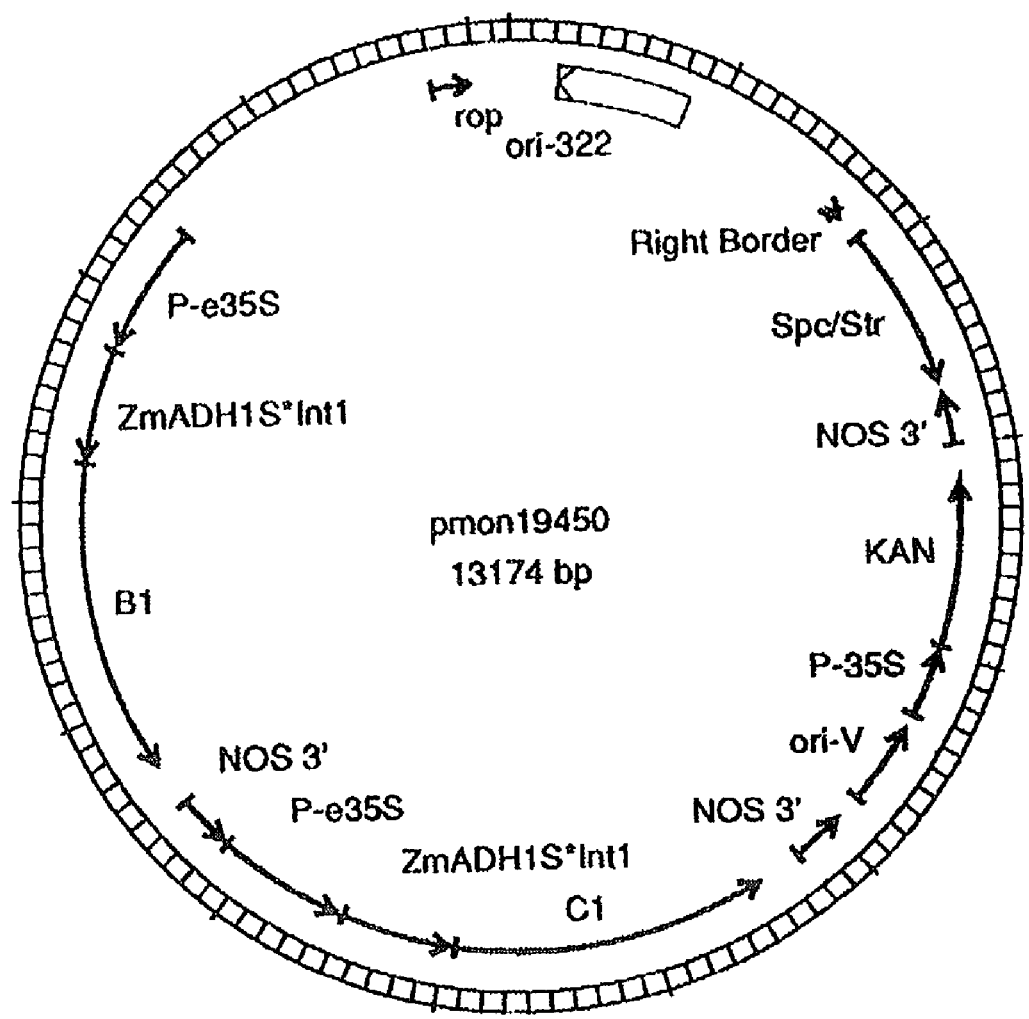
FIG. 10 shows the structure of pMON19450.

One may also insert genes affecting traits in wheat such as tolerance to herbicides for herbicide resistance, tolerance to drought and high salinity, and tolerance to cold and heat stresses. Genes increasing yield of wheat plants, genes used for male sterility for the production of hybrid wheat, and genes influencing germination could also be introduced into binary plant transformation vectors for *Agrobacterium*-mediated transformation producing wheat plants expressing traits of the desired phenotype. Examples of plasmids useful for inserting genes include pMON25457 (FIG. 7), pMON30053 (FIG. 8), pMON30052 (FIG. 9), and pMON19450 (FIG.10).

6. References

The references listed below and all references cited herein are incorporated herein by reference to the extent that they supplement, explain, provide a background for, or teach methodology, techniques, and/or compositions employed herein.

U. S. Pat. No. 5,179,022.
Intl. Pat. Appl. Publ. No. WO 91/02071.
Intl. Pat. Appl. Publ. No. WO 92/06205.
Intl. Pat. Appl. Publ. No. WO 93/18168.
Intl. Pat. Appl. Publ. No. WO 94/0077.
Intl. Pat. Appl. Publ. No. WO 94/00583.
Intl. Pat. Appl. Publ. No. WO 95/06722.
Barcelo et al., *Plant J.,* 5:583–592, 1994.
Becker et al., *Plant J.,* 5:299–307, 1994.
Bevan et al., *Nature,* 303:209, 1983
Chan et al., *Plant Cell Physiol.,* 33(5):577–583, 1992.
Chan et al., *Plant Mol. Biol.,* 22(3):491–506, 1993.
Chan et al., *Plant Physiol.,* (Rockville) 108 (2 Suppl.) 115, Abstr. Annu. Meet. Amer. Soc. Plant Physiol., Charlotte, N.C., 1995.
Chen and Dale, *Transgenic Res.,* 1(2):93–100, 1992.
Chilton, *Proc. Natl. Acad. Sci. USA,* 90(8):3119–3120, 1993.
Christou et al., *Plant Physiol.,* 87:671–674, 1988.
Christou et al., *Bio/Technology,* 9:957–962, 1991.
Conger et al., *Plant Cell Rep.,* 6:345–347, 1987.
Conner and Dommisse, *Int. J. Plant Sci.,* 153:550–555, 1992.
Creissen et al., *Plant Cell Rep.,* 8(11):680–683, 1990.
Datta et al., *Bio-Technology,* 8:736–740, 1990.
Davey et al., *J. Exp. Bot.,* 42:1129–1169, 1991.
De la Pena et al., *Nature,* 325:274–276, 1987.
Dekeyser et al., *Plant Physiol.,* 90:217–223, 1989.
Delbreil et al., *Plant Cell Rep.,* 12(3):129–132, 1993.
Della-Cioppa et al., *Bio/Technology,* 5:579–584, 1987.
Deng et al., *Sci. China Ser B Chem. Life Sci. Earth Sci.,* 33(1):27–34, 1990.
Du et al, *Genet. Manip. Plants,* 5:8–12, 1989.
Fromm et al., *Proc. Natl. Acad. Sci. USA,* 82:5824–5828, 1985.
Fromm et al, *Nature,* 319:791–793, 1986.
Fromm et al, *Bio/Technology,* 8:833–839, 1990.
Godwin and Chikwamba, xiii-174, Plenum Press: New York, N.Y.
Gordon-Kamm et al., *Plant Cell,* 2:603–618, 1990.
Gould et al., *Plant Physiol.,* 95(2):426–434, 1991.
Graves and Goldman, *Plant Mol Biol.,* 7(1):43–50, 1986.
Grimsley et al., *Nature,* 325:177–179, 1987.
Hayakawa et al, *Proc. Natl Acad. Sci. USA,* 89:9865–9869, 1992.
Herrera-Estrella et al., *Nature,* 303:209, 1983.
Hess et al., *Plant Sci.,* 72(2):233–244, 1990.
Hiei, Y, *Plant J.,* 6(2):271–282, 1994.
Hood et al., *Plant Physiol.,* 105(1 Suppl.), 114, 1994.
Ishida et al., *Plant Physiol.,* (Rockville) 108 (2 Suppl.) 114, Abstr. Annu. Meet. Amer. Soc. Plant Physiol., Charlotte, N.C., 1995.
Ishida, Y, et al., *Nature Biotech.,* 745–750, 1996.
Jaehne et al., *Euphytica,* 85:1–3:35–44, 1995.
Jefferson, *Plant Mol. Biol. Rep.,* 5:387–405, 1987.
Jefferson et al., *EMBO J.,* 6:3901–3907, 1987.
Kasha et al., *Gene Manip. Plant Improv. II,* 213–239, 1990.
Klee et al., *Bio/Technology,* 3:637, 1985.
Knutson et al., *Proc. Natl. Acad. Sci. USA,* 89:2624–2628, 1992.
Kornienko et al., *Pushchino,* 20–22, *noyabrya, Tezisy dokladov,* 20:21, 128–129, 1991.
Langridge et al., *Plant J.,* 2(4):631–638, 1992.
Li et al., *Sci. Shina Ser B Chem. Life Sci. Earth Sci.,* 34(1):54–63, 1991.
Liu et al., *Plant Mol. Biol.,* 20(6):1071–1087, 1992.
Luo and Wu, *Plant Mol. Biol. Rep.,* 6:165–174, 1988.
Mahalakshmi and Khurana, *J. Plant Biochem. Biotech.,* 4(2):55–59, 1995.
May et al., *Bio/Technology,* 13:486–492, 1995.
McElroy et al., *Mol. Gen. Genet.* 231:150–160, 1991.
Miljus-Djukic et al., *Plant Cell Tissue Organ Culture,* 29(2): 106–108, 1992.
Miller, Cold Spring Harbor Laboratory Press, Cold Spring Harbor, N.Y., 1972.
Mooney and Doodwin, *Plant Cell Tissue Organ Culture,* 25:209–218, 1991.
Mursahige and Skoog, *Physiol. Plant,* 15:473–497, 1962.
Nehra et al., *Plant J.,* 5:285–297, 1994.
Paszkowski et al., *EMBO J.,* 3:2717–2722, 1984.
Paszkowski et al., *Plant Mol. Biol.,* 6:303–312, 1986.
Picard et al., VIIth International Wheat Genetics Symposium, University of Cambridge, 779:781, 1988.
Piorer et al., *Science,* 256:520–523, 1992.
Potrykus, I., *Bio/Technology,* 8:535–543, 1990.
Raineri et al., *Bio/Technology,* 8:33, 1990.
Raineri et al., *Proc. Natl. Acad. Sci. USA,* 90(8):3549–3553, 1993.
"Report on the Use of Antibiotic Resistance Markers in Genetically Modified Food Organisms," Advisory Committee on Novel Foods and Processes, July 1994.

What is claimed is:

1. A method for producing a fertile transgenic wheat plant, comprising the steps of:
   (a) establishing a regenerable culture from a wheat plant to be transformed; wherein the regenerable culture comprises:
      i) an immature embryo; wherein the immature embryo is pre-cultured and non-injured or;
      ii) an embryogenic callus tissue; wherein the embryogenic callus tissue is prepared from immature embryo;
   (b) introducing a DNA composition comprising a genetic component one desires to introduce into the genome of said wheat plant, by *Agrobacterium* transformation;
   (c) identifying or selecting a transformed cell line; and
   (d) regenerating a fertile transgenic wheat plant therefrom, wherein said DNA is transmitted through a complete sexual cycle of said transgenic plant to its progeny, wherein said progeny comprises a selectable or screenable marker gene, and wherein said marker gene is chromosomally integrated.

2. The method of claim 1, wherein at least two exogenous genes are positioned on the same DNA segment, and said regenerable culture is transformed with said segment.

3. The method of claim 1, wherein said *Agrobacterium* is *A. tumefaciens* C58.

4. The method of claim 1, wherein said culture comprises an immature embryo.

5. A method for producing a transgenic wheat plant, comprising the steps of
   (a) establishing a regenerable culture from a wheat plant to be transformed; wherein the regenerable culture comprises:
      i) an immature embryo; wherein the immature embryo is pre-cultured and non-injured or;
      ii) an embryogenic callus tissue; wherein the embryogenic callus tissue is prepared from immature embryo;

(b) transforming said culture with an *Agrobacterium* comprising a DNA composition comprising a genetic component one desires to introduce into the genome of said wheat plant;

(c) identifying or selecting a transformed cell line; and (d) regenerating a transgenic wheat plant therefrom.

6. The method of claim 1 or 5, wherein said DNA comprises an nptII gene.

7. The method of claim 5, wherein said *A. Agrobacterium* is *A. tumefaciens* C58.

8. The method of claim 1 wherein said culture comprises embryogenic callus.

9. The method of claim 1 wherein the *Agrobacterium* transformation comprises use of *Agrobacterium* in an inoculation medium comprising a surfactant.

10. The method of claim 5 wherein the *Agrobacterium* transformation comprises use of *Agrobacterium* in an inoculation medium comprising a surfactant.

* * * * *